United States Patent
Yin et al.

(10) Patent No.: US 12,173,292 B2
(45) Date of Patent: Dec. 24, 2024

(54) CONTROLLING BACTERIAL BIOFILMS

(71) Applicants: LANXESS Corporation, Pittsburgh, PA (US); THE PENN STATE RESEARCH FOUNDATION, University Park, PA (US)

(72) Inventors: Bei Yin, Wilmington, DE (US); Thomas K. Wood, Port Matilda, PA (US)

(73) Assignees: LANXESS Corporation, Pittsburgh, PA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 17/884,675

(22) Filed: Aug. 10, 2022

(65) Prior Publication Data

US 2022/0389435 A1 Dec. 8, 2022

Related U.S. Application Data

(63) Continuation of application No. 16/795,726, filed on Feb. 20, 2020, now abandoned.

(60) Provisional application No. 62/808,786, filed on Feb. 21, 2019.

(51) Int. Cl.
*C12N 15/74* (2006.01)
*C12Q 1/02* (2006.01)
*C12Q 1/18* (2006.01)

(52) U.S. Cl.
CPC ............. *C12N 15/74* (2013.01); *C12Q 1/025* (2013.01); *C12Q 1/18* (2013.01)

(58) Field of Classification Search
CPC .................................................... C12N 15/74
See application file for complete search history.

*Primary Examiner* — Albert M Navarro

(57) ABSTRACT

Methods of controlling bacteria cells are disclosed. These methods comprise upregulating expression of a DVU2956 sigma 54-dependent enhancer-binding protein (EBP) in bacteria cells, resulting in (i) dispersing a biofilm of the cells or reducing biofilm formation by the cells, and/or (ii) reducing hydrogen sulfide formation by the cells. Further disclosed are methods of identifying compounds for controlling bacteria cells as in (i) and/or (ii) above. Polynucleotides and cells are disclosed that can optionally be used to practice compound identification methods.

8 Claims, 3 Drawing Sheets

Figure 1:
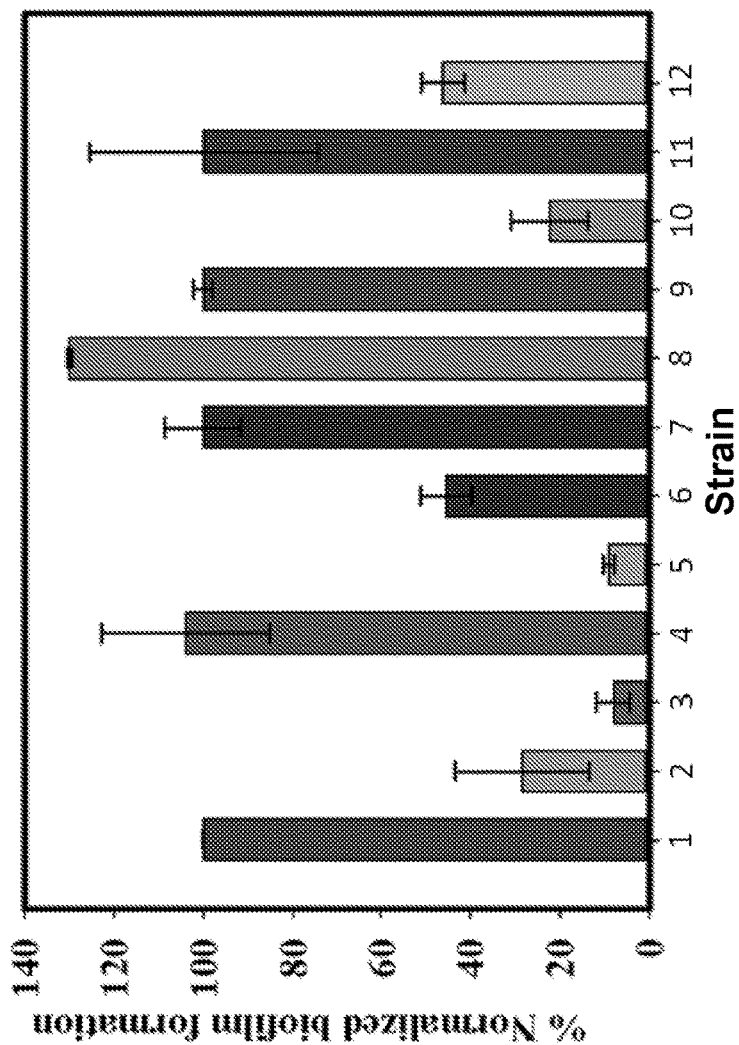

Specification includes a Sequence Listing.

```
                               SEQUENCE LISTING

Sequence total quantity: 21
SEQ ID NO: 1            moltype = DNA  length = 1038
FEATURE                 Location/Qualifiers
source                  1..1038
                        mol_type = other DNA
                        organism = Desulfovibrio vulgaris Hildenborough
SEQUENCE: 1
atgagcggca aaaaattacc gcatagcggc aattctcttc ccattgaggg gacggtatcg   60
ccccagcgcg aaacgcttca gaacggaacg gacttcctgc ttctgtcagg cgtcatgcaa   120
aggttgcggg tgcttgcgtc gcaagtcgcc tcctccgatg cgccagtgct cattcatggt   180
gagacgggaa cgggcaagga actcttcgcc cgtctcatcc acgatatggg cattcgagcc   240
aaaaagcctt ttgtggcagt caattgcgga gtccacgagg gtgagctctt cgccgacaag   300
ttcttcggcc atgagcaggg ggcgttcacc ggggcgcaca gaatgagtca gggatgtttc   360
gagctcgctt cggaggggac gctcttcctt gacgaagtgg gcgagatacc cggtgccaat   420
caggcggatt tcctgcgggt gctggaagag aagcgtttca ggcgcatcgg cgggcagcgt   480
gacatcccgt ttcaggcgcg tatcgtcgcc gcctcgaacc gtgatttgca ggagatggtg   540
gggcagggc agttcagggc cgacctcttc tacaggctca atgtcattcc cgtggtcctt   600
ccgcccttgc gtgcccgcaa ggaggaggtc gtgccgctgg cacggcattt cctgacccat   660
tatggcgaca agtaccatcg gcccggtgtc cgtttcgccc cggagacgga acaggcgctg   720
gcggcgtacc agtggccggg gaacgtgcgc gagctcaaga atcttgtgga acgcatcgcg   780
ttgctcgcgc cggaaggcgt tctcgggcct gaacatctgc cgcttgagtt gcgttcagcc   840
gctgcggtgg aggtgggggt gccccacgag gtgccggaag acctgagcct cgaccgggcc   900
agacgagagg ccgaggtgcg cgtcatcctc aaggccatgc gcgccactgg cggcaacaag   960
ggcgaggcgg cccgcctgct gggagtgagc ccgcgtaccc tgcgctacaa gtttgcggag   1020
tatgcgttgc gattctga                                                1038

SEQ ID NO: 2            moltype = AA  length = 345
FEATURE                 Location/Qualifiers
source                  1..345
                        mol_type = protein
                        organism = Desulfovibrio vulgaris Hildenborough
SEQUENCE: 2
MSGKKLPHSG NSLPIEGTVS PQRETLQNGT DFLLLSGVMQ RLRVLASQVA SSDAPVLIHG   60
ETGTGKELFA RLIHDMGIRA KKPFVAVNCG VHEGELFADK FFGHEQGAFT GAHRMSQGCF   120
ELASEGTLFL DEVGEIPGAN QADFLRVLEE KRFRRIGGQR DIPFQARIVA ASNRDLQEMV   180
GQGQFRADLF YRLNVIPVVL PPLRARKEEV VPLARHFLTH YGDKYHRPGV RFAPETEQAL   240
AAYQWPGNVR ELKNLVERIA LLAPEGVLGP EHLPLELRSA AAVEVGVPHE VPEDLSLDRA   300
RREAEVRVIL KAMRATGGNK GEAARLLGVS PRTLRYKFAE YALRF                  345

SEQ ID NO: 3            moltype = DNA  length = 1425
FEATURE                 Location/Qualifiers
source                  1..1425
                        mol_type = other DNA
                        organism = Desulfovibrio vulgaris Hildenborough
SEQUENCE: 3
```

```
atgaagcaag catccctgcc agcaggtgcc cggatagccg ggctcgtcgg gcgcgaactc    60
gcgctcggcc cggtcttcga cgccatcccc accgggttgg cggtgctcga tgccgacctg   120
cgcatatgcc tgatgaaccg cgcccttgag accatgacgg ggttcaccac cgccgaggtg   180
gcgggcatcc cctgccggca tgtccttcgg gccagcgtat gcctgcaccg ctgccctacc   240
cgcaccgctg tctgcgatgc caccgacggc aacgcgccat gccatgcaca agaaggcgac   300
ctgctcaacc gccatcgccg ccgcattccc gtgcgcctga ccctcgcccc tctccatgat   360
gcgcagggc agctgtgcgg ctggctgcat accgccgaag acctttcgct cgtccgtgag   420
cttgaagaac ggtgcagcaa ggggcaggca tccgggccac tggtggggcg cagcgtggtg   480
atggaggaac tcttccgtac cgtgcaggcc cttgcccaga ccgagaccc cgtgctcatc   540
acgggcgaga cgggcacagg caaggacgcc gtggccgaga ccatccacaa ggcatcaccg   600
cgcggtcgcg aaccgttcgt caaggccagc tgtcatccc ttcccgattt tctggtggag   660
tccgaactgt tcgccaccg caagggcgcg ttccccgggg ccgaagagga caagcccggc   720
cgtttcagga tggcacaggg cggtacgttg tgcctgtccg agtgggcga cctgccccc   780
gccatgcagg gacggctcgt gacgttcctc gacgagggac tggtctggcc gtggggcgcc   840
acagaccccg tcaggtgcga cgtgcgcctc tcgttgcca gcaacctcga cctggaggcc   900
atggtcgctt ccggaaggct gcgcgaagac ctctacagca gactggcagc cgtgcgcatc   960
cacctgcccc cgctacgcga acggggcgaa gacctcgagt tcctgctcag ccactacctt  1020
gcccatttcg ccgccagatt gcgcaagacc atacacggt tctccggcaa atctctgcgc  1080
gtgctgcttg cctacggctt tccgggcaac gtgcgtgagc tcaagaacat cgtcgagtac  1140
gccgcgaccc tgtgtacggg cgaggtcgtc atgccctcgc acctgccggc ctacctcttc  1200
cacacgcgtc cggcagccgc accccgcgt gccatcgaac gcgacacccc caagggtgcc  1260
gccgaagcgg aggcatcagc ccgaccgcc gtcgtcgaca tcgaacgcgc tctcatcgtg  1320
gacgcactgg cacgcgccgg aaaccgcaag ggcgaggccg cccgcatcct cggctgggc  1380
agaagcaccc tgtggcgcaa gatgaaacag ttcggactgg agtga               1425

SEQ ID NO: 4             moltype = AA   length = 474
FEATURE                  Location/Qualifiers
source                   1..474
                         mol_type = protein
                         organism = Desulfovibrio vulgaris Hildenborough
SEQUENCE: 4
MKQASLPAGA RIAGLVGREL ALGPVFDAIP TGLAVLDADL RICLMNRALE TMTGFTTAEV    60
AGIPCRHVLR ASVCLHRCPT RTAVCDATGG NAPCHAQEGD LLNRHRRRIP VRLTLAPLHD   120
AQGQLCGWLH TAEDLSLVRE LEERCSKGQA SGPLVGRSVV MEELFRTVQA LAQTETPVLI   180
TGETGTGKDA VAETIHKASP RGREPFVKAS LSSLPDFLVE SELFGHRKGA FPGAEEDKPG   240
RRFMAQGGTL CLSELGDLPP AMQGRLVTFL DEGLVWPVGA TDPVRCDVRL LVASNLDLEA   300
MVASGRLRED LYSRLAAVRI HLPPLRERGE DLEFLLSHYL AHFAARLRKT IHGFSGKSLR   360
VLLAYGFPGN VRELKNIVEY AATLCTGEVV MPSHLPAYLF HTRPAAAPPR AIERDTPKGA   420
AEDEASARSS VVDLERRLIV DALARAGNRK GEAARILGWG RSTLWRKMKQ FGLE         474

SEQ ID NO: 5             moltype = DNA   length = 348
FEATURE                  Location/Qualifiers
source                   1..348
                         mol_type = other DNA
                         organism = Desulfovibrio vulgaris Hildenborough
SEQUENCE: 5
atgcccgcga cactgctcat ccccctctac cgcgacgagg tcgcaccacg cttcgacctc    60
gccggtgaag tgctgctcgt gacccctcgac gccgaaggga ccgagacgga acgctccagc   120
gtcgtgcttg cccatgcctc ttccgaggac atctgccgca tggcactgga agagaaggtc   180
cgcaccgtca tatgcagcgg cattgacgag gaattctggc agtacctgcg ctggaagcgt   240
attgaggtca tcgacaacgt catcggcccg gtcgaggagg cgttgcgacg tcatgcggcc   300
ggaatgctcc gttcaggcga catcctcttc acagggagg gggcatga                 348

SEQ ID NO: 6             moltype = AA   length = 115
FEATURE                  Location/Qualifiers
source                   1..115
                         mol_type = protein
                         organism = Desulfovibrio vulgaris Hildenborough
SEQUENCE: 6
MPATLLIPLY RDEVAPRFDL AGEVLLVTLD AEGTETERSS VVLAHASSED ICRMALEEKV    60
RTVICSGIDE EFWQYLRWKR IEVIDNVIGP VEEALRRHAA GMLRSGDILF HREGA         115

SEQ ID NO: 7             moltype = DNA   length = 1734
FEATURE                  Location/Qualifiers
source                   1..1734
                         mol_type = other DNA
                         organism = Desulfovibrio vulgaris Hildenborough
SEQUENCE: 7
atgaagaacc cgctaggcac catgctctcg cgtctgcgct cggtgttcga cgttccggat    60
gagatcgcgc cggaacgcta ccgcatgctg cggcgcaaga taacgctgct catgacggcg   120
gtgtcggttc tgccgctgct catcctcacc gccgtaagct accaccagta ccagagcacc   180
ctcacccgcg aaatcgtcac cccgtgcgg gcgctggtga caagacccg ccactcgttc   240
gaactgttcc ttgccgaacg gtcgtccacc gtgagccttc tcgccaagac ctattccatg   300
gcggaacttt ccgacgagaa gaacctcaac cgcatcctcc tcgcgctcaa gggcgagttc   360
cccggcttcg tcgacctcgg ggtcatcgac ggcaggggcg tgcaggtggg ctatgtcggg   420
ccgtacgacg tacgggggaa gaactactcc gaggcggact ggtacaaccg caccgcgtg   480
aagggtgtct acatcagcga cgtgttcatg ggtttcaggc gctttccgca catgccatc   540
gccgtgcagc gcatgaaccc cgacggcagt cgtggatgc ttcgcgccac catcgagacc   600
acgcagttcg acaggctcat cgcctccatg gggctcgacc cggagagtga cgcctttcctc   660
```

-continued

```
atcaacaccg ccggagtact ccagaccaac tcgcgcttct acggcaatgt gctcgacgtg    720
atgcccatgc cggtgcccca cctgagctac gagccctcga tcatcgacac ggaagatccc    780
gagggcaggc agattttcct ctcttcagcc tttctgcaga atgccgactt cgccatcgtg    840
gcggtcaagc ccaagaccga gatcctgcgc cgtggacat cgctgcgcag cgaccttctg     900
attttcgtcg ccttcagtgt cgccctcatc atctcagcgg ccttcggctt caccgacatg    960
ctcgtacgac gcatgcgcga cagcgacgaa cggcgcatcg ccgccttcgt gcagatagag   1020
cacacccaga aactctcctc catcggcagg ctggcggcgg cgtcgcccca cgaaatcaac   1080
aaccccctcg ccatcatcaa cgaaaaggcg ggccttgcgg cagacctcat cgcgctttcg   1140
caggactttc cgcagaaaga acgcttctcg gccatcgtcg aggccgccat cgcgttctgc   1200
gaccgttgcc ggtccatcac gcacaggctt ctcggcttct cgcgccgcat ggacgccacc   1260
tacgagcaac tcgacgtcaa cggcatcctc aaagagacca tgagcttcct ggaacaggag   1320
gccgtgcacc gttccatcac catcggcacc agtctcgacg cggggctgcc acgcatcacc   1380
tccgacaggg ggcagttgca gcaggtcttc ctcaacatca tcaacaacgc cttcgccgca   1440
gtgcaggacg gtggttccgt gacgctcacc acgttcgcag cggacggcgg catggtgggc   1500
gtctcgatac aggacaacgg aaagggcatg tctgaagaag tgcagcggca catcttcgaa   1560
ccgttcttca ccaccaagaa gacggcgggg acgggcctag gcatgttcat cacctacggg   1620
atcatcaagc gactgggcgg agagatcggc atcaacagca gggagggcgt tggcaccacc   1680
gtcaccgtct acctgccgca ggacgcgccc gcaccgcaat cgctggagaa ctag         1734

SEQ ID NO: 8                moltype = AA  length = 577
FEATURE                     Location/Qualifiers
source                      1..577
                            mol_type = protein
                            organism = Desulfovibrio vulgaris Hildenborough
SEQUENCE: 8
MKNPLGTMLS RLRSVFDVPD EIAPERYRML RRKITLLMTA VSVLPLLILT AVSYHQYQST     60
LTREIVTPVR ALVNKTRHSF ELFLAERSST VSLLAKTYSM AELSDEKNLN RIFLALKGEF    120
PGFVDLGVID GRGVQVGYVG PYDVRGKNYS EADWYNRTRV KGVYISDVFM GFRRFPHIAI    180
AVQRMNPDGS SWMLRATIET TQFDRLIASM GLDPESDAFL INTAGVLQTN SRFYGNVLDV    240
MPMPVPHLSY EPSIIDTEDP EGRQIFLSSA FLQNADFAIV AVKPKTEILR PWTSLRSDLL    300
IFVAFSVALI ISAAFGFTDM LVRRMRDSDE RRIAAFVQIE HTQKLSSIGR LAAGVAHEIN    360
NPLAIINEKA GLAADLIALS QDFPQKERFS AIVEAISRSV DRCRSITHRL LGFSRRMDAT    420
YEQLDVNGIL KETMSFLEQE AVHRSITIGT SLDAGLPRIT SDRGQLQQVF LNIINNAFAA    480
VQDGGSVTLT TFAADGGMVG VSIQDNGKGM SEEVQRHIFE PFFTTKKTAG TGLGMFITYG    540
IIKRLGGEIG INSREGVGTT VTVYLPQDAP APQSLEN                             577

SEQ ID NO: 9                moltype = DNA  length = 660
FEATURE                     Location/Qualifiers
source                      1..660
                            mol_type = other DNA
                            organism = Desulfovibrio vulgaris Hildenborough
SEQUENCE: 9
atgcgcgaga acgcctgtgt gggatgtctc accgcatccg catcgcacga actgcagaac     60
gccctcgcgg tcatccgcga atctgccggc ctgatgcaag acctcatcgc ccttggcgga    120
gagaacatcc cccggcgtga gcgcatcgtc gaactgctct ctctcatcca gcagcaggtg    180
gcgcgcggc gcgagttggc ggggggggctc aacacccttg gtcacgcatg gaagaggat     240
gacggcgacc tcgcccgcat cctcgaagag ttcgtcatcc ttgccgggcg catgggcagg    300
atgcgttccg tcaccgtggg actggcaccg ggcgaaagcg gcttgcgcgc gccgagtgcg    360
gggcttgcct tgcgagtgct gctgttcgac ctttttgcaga cctgccttga agaggctccc    420
ggttgcgcgc tcaccttcgc cccggcaagg cgcgacggca ttcccggaat acatctgcga    480
gtaggactgg cacgttgcga cgcgactaca gactgactgc gccgactcga ctgcgcaactt   540
gcccgtctcg gagcccgtaa ggagcccgac aacgggcacg gaacgcccgc aagggacgaa    600
ccggacggag tgttgtacta tttcacggcc tgtccctctg caacagggca cagggcatag    660

SEQ ID NO: 10               moltype = AA  length = 219
FEATURE                     Location/Qualifiers
source                      1..219
                            mol_type = protein
                            organism = Desulfovibrio vulgaris Hildenborough
SEQUENCE: 10
MRENACVGCL TASASHELQN ALAVIRESAG LMQDLIALGG ENIPRRERIV ELLSLIQQQV     60
ARGGELAGGL NTLGHAWEED DGDLARILEE FVILAGRMGR MRSVTVGLAP GESGLRAPSA    120
GLALRVLLFD LLQTCLEEAP GCALTFAPAR RDGIPGIHLR VGLARCDATT DVLRRLDAQL    180
ARLGARKEPD NGHGTPARDE PDGVLYYFTA CPSATGHRA                           219

SEQ ID NO: 11               moltype =  length =
SEQUENCE: 11
000

SEQ ID NO: 12               moltype = DNA  length = 86
FEATURE                     Location/Qualifiers
misc_feature                1..86
                            note = dvu2956 gene regulatory sequence
source                      1..86
                            mol_type = other DNA
                            organism = Desulfovibrio vulgaris Hildenborough
SEQUENCE: 12
aatgcttttt gtcgtggact tgtgacatgt ataacaagtt ccgtgccagc ggtgagcgct     60
tgccgttcca cggattacaa gctatc                                         86
```

| SEQ ID NO: 13 | moltype = DNA length = 41 |
|---|---|
| FEATURE | Location/Qualifiers |
| misc_feature | 1..41 |
| | note = predicted dvu2956 gene promoter sequence (Pdvu2956) |
| source | 1..41 |
| | mol_type = other DNA |
| | organism = Desulfovibrio vulgaris Hildenborough |

SEQUENCE: 13
```
aatgcttttt gtcgtggact tgtgacatgt ataacaagtt c                41
```

| SEQ ID NO: 14 | moltype = DNA length = 45 |
|---|---|
| FEATURE | Location/Qualifiers |
| misc_feature | 1..45 |
| | note = predicted dvu2956 gene 5'-UTR sequence |
| source | 1..45 |
| | mol_type = other DNA |
| | organism = Desulfovibrio vulgaris Hildenborough |

SEQUENCE: 14
```
cgtgccagcg gtgagcgctt gccgttccac ggattacaag ctatc            45
```

| SEQ ID NO: 15 | moltype = DNA length = 24 |
|---|---|
| FEATURE | Location/Qualifiers |
| misc_feature | 1..24 |
| | note = Synthetic ribosome binding site (sRBS) |
| source | 1..24 |
| | mol_type = other DNA |
| | organism = synthetic construct |

SEQUENCE: 15
```
gcgagataaa aaaaggagga cttt                                   24
```

| SEQ ID NO: 16 | moltype = DNA length = 711 |
|---|---|
| FEATURE | Location/Qualifiers |
| misc_feature | 1..711 |
| | note = Codon-optimized sequence encoding mNeonGreen |
| source | 1..711 |
| | mol_type = other DNA |
| | organism = synthetic construct |

SEQUENCE: 16
```
atggtgagca agggcgagga ggataacatg gcctctctcc cagcgacaca tgagttacac   60
atctttggct ccatcaacgg tgtggacttt gacatggtgg gtcagggcac cggcaatcca  120
aatgatggtt atgaggagtt aaacctgaag tccaccaagg gtgacctcca gttctccccc  180
tggattctgg tccctcatat cgggtatggc ttccatcagt acctgcccta ccctgacggg  240
atgtcgcctt tccaggccgc catggtagat ggctccggat accaagtcca tcgcacaatg  300
cagtttgaag atggtgcctc ccttactgtt aactaccgct cacctacga gggaagccac   360
atcaaaggag aggcccaggt gaaggggact ggtttccctg ctgacggtcc tgtgatgacc  420
aactcgctga ccgctgcgga ctggtgcagg tcgaagaaga cttaccccaa cgacaaaacc  480
atcatcagta cctttaagtg gagttacacc actggaaatg gcaagcgcta ccggagcact  540
gcgcggacca cctacacctt tgccaagcca atgcgggcta actatctgaa gaaccagccg  600
atgtacgtgt ccgtaagac ggagctcaag cactccaaga ccgagctcaa cttcaaggag   660
tggcaaaagg ccttttaccga tgtgatgggc atggacgagc tgtacaagta a           711
```

| SEQ ID NO: 17 | moltype = DNA length = 821 |
|---|---|
| FEATURE | Location/Qualifiers |
| misc_feature | 1..821 |
| | note = Pdvu2956-5' UTR-sRBS-mNeonGreen cassette. |
| source | 1..821 |
| | mol_type = other DNA |
| | organism = synthetic construct |

SEQUENCE: 17
```
aatgcttttt gtcgtggact tgtgacatgt ataacaagtt ccgtgccagc ggtgagcgct   60
tgccgttcca cggattacaa gctatcgcga gataaaaaaa ggaggacttt atggtgagca  120
agggcgagga ggataacatg gcctctctcc cagcgacaca tgagttacac atctttggct  180
ccatcaacgg tgtggacttt gacatggtgg gtcagggcac cggcaatcca aatgatggtt  240
atgaggagtt aaacctgaag tccaccaagg gtgacctcca gttctccccc tggattctgg  300
tccctcatat cgggtatggc ttccatcagt acctgcccta ccctgacggg atgtcgcctt  360
tccaggccgc catggtagat ggctccggat accaagtcca tcgcacaatg cagtttgaag  420
atggtgcctc ccttactgtt aactaccgct cacctacga gggaagccac atcaaaggag  480
aggcccaggt gaaggggact ggtttccctg ctgacggtcc tgtgatgacc aactcgctga  540
ccgctgcgga ctggtgcagg tcgaagaaga cttaccccaa cgacaaaacc atcatcagta  600
cctttaagtg gagttacacc actggaaatg gcaagcgcta ccggagcact gcgcggacca  660
cctacacctt tgccaagcca atgcgggcta actatctgaa gaaccagccg atgtacgtgt  720
ccgtaagac ggagctcaag cactccaaga ccgagctcaa cttcaaggag tggcaaaagg   780
ccttttaccga tgtgatgggc atggacgagc tgtacaagta a                     821
```

| SEQ ID NO: 18 | moltype = AA length = 6 |
|---|---|
| FEATURE | Location/Qualifiers |
| source | 1..6 |
| | mol_type = protein |

```
                        organism = Desulfovibrio vulgaris Hildenborough
SEQUENCE: 18
GAFTGA                                                                  6

SEQ ID NO: 19           moltype = AA  length = 41
FEATURE                 Location/Qualifiers
source                  1..41
                        mol_type = protein
                        organism = Desulfovibrio vulgaris Hildenborough
SEQUENCE: 19
RREAEVRVIL KAMRATGGNK GEAARLLGVS PRTLRYKFAE Y                           41

SEQ ID NO: 20           moltype = AA  length = 9
FEATURE                 Location/Qualifiers
source                  1..9
                        mol_type = protein
                        organism = Desulfovibrio vulgaris Hildenborough
SEQUENCE: 20
KGEAARLLG                                                               9

SEQ ID NO: 21           moltype =    length =
SEQUENCE: 21
000
```

CONTROLLING BACTERIAL BIOFILMS

This application is a continuation of U.S. patent application Ser. No. 16/795,726 (filed Feb. 2, 2020), which claims the benefit of U.S. Provisional Application No. 62/808,786 (filed Feb. 21, 2019), which is incorporated herein by reference in its entirety.

FIELD

The present disclosure is in the field of molecular biology and microbiology. The disclosure pertains to methods of controlling bacterial biofilms, for example.

REFERENCE TO SEQUENCE LISTING SUBMITTED ELECTRONICALLY

The contents of the electronic sequence listing (G1421US00_DI83116.xml; Size: 29 KB; Original Date of Creation: Feb. 21, 2019, and Converted to ST.26 Format: Aug. 9, 2022) is herein incorporated by reference in its entirety.

BACKGROUND

Metabolic activity of microbes can cause problems in a broad array of industries. For example, bacteria can create microbiologically influenced corrosion (MIC) on metal surfaces of equipment and cause degradation of polymer additives. Also, biofilms formed by both aerobic and anaerobic bacteria can physically plug oil and gas pipelines and water purification systems, as well as reduce the efficiency of pumps and heat transfer systems. Although aerobic and anaerobic bacteria coexist in many environments, contaminant aerobic bacteria are more often found topside (i.e., near the surface) in injection water, produced water, and functional water-based fluids such as drilling muds, completion or workover fluids, stimulation fluids, fracturing fluids, and hydrotest fluids. Contaminant anaerobic bacteria, on the other hand, are most commonly found downhole (i.e., underground) in oil or gas reservoirs, produced fluids, deaeration towers, transmission pipelines, the water bottoms of oil and gas storage tanks, and near bore areas.

A particular type of bacteria known as sulfate-reducing bacteria (SRB) produce hydrogen sulfide, which can sour oil and gas, and corrode pipelines and storage tanks. SRB, which are the major cause of biocorrosion of iron and other metals used in industry, incur enormous global economic costs (Enning and Garrelfs, 2014, *Appl. Environ. Microbiol.* 80:1226-1236). Hence, controlling SRB biofilms by preventing their formation and promoting their dispersal is important.

SRB biofilms contain protein (Clark et al., 2007, *Environ. Microbiol.* 9:2844-2854) and exopolysaccharide (EPS) containing polymers of mannose, N-acetyl-beta-D-galactosamine (GalNAc) and fucose (Poosarla et al., 2017, *Environ. Microbiol. Rep.* 9:779-787). Based on this structure, dispersal of SRB biofilms has been shown by treatment with proteases (Clark et al., 2007) and glycoside hydrolases (Zhu et al., 2018, *Environ. Microbiol.* 20:2026-2037).

In regard to regulation of SRB biofilm formation, gene expression in *D. vulgaris* biofilms growing on steel was studied using microarrays, finding that some discontinuous distributed EPS biosynthesis genes were induced (Zhang et al., 2007, *Appl. Microbiol. Biotechnol.* 76:447-457). In addition, gene and protein expression profiles of SRB biofilms as examined by microarrays and iTRAQ® identified some unknown extracellular proteins as important for biofilm formation (Clark et al., 2012, *BMC Genomics* 13:138). Another report focused on differential gene expression in biofilm cells and planktonic cells at the single cell level (Qi et al., 2016, *Front. Microbiol.* 7:597); that study found that EPS biosynthesis gene dvu0281 and ferric iron uptake and storage genes dvu1340 and dvu1397 were induced in biofilms, while certain genes including those involved in energy metabolism (dvu0434 and dvu0588), stress response (dvu2410), and iron transportation (dvu2571) were repressed in biofilms.

Despite this work, little is known with respect to regulation of biofilm formation and dispersal by bacteria such as SRB. In providing further insights in this area, the instant disclosure provides new modes of controlling bacterial biofilms.

SUMMARY

In one embodiment, the present disclosure concerns a method of controlling bacteria cells. This method comprises upregulating expression of a DVU2956 sigma 54-dependent enhancer-binding protein (EBP) in the bacteria cells, thereby (i) dispersing a biofilm of the cells or reducing biofilm formation by the cells, and/or (ii) reducing hydrogen sulfide formation by the cells.

In another embodiment, the present disclosure concerns a method of identifying a candidate compound for controlling bacteria cells. This method comprises: (a) providing bacteria cells comprising a polynucleotide that comprises (i) a DVU2956 sigma 54-dependent enhancer-binding protein (EBP) regulatory sequence operably linked to (ii) a nucleotide sequence; (b) contacting the bacteria cells of step (a) with at least one test compound; and (c) determining whether expression of the nucleotide sequence by the bacteria cells of step (b) is upregulated, wherein such upregulation indicates that the test compound is a candidate compound for (i) controlling biofilm maintenance or biofilm formation by the bacteria cells or other bacteria cells, and/or (ii) reducing hydrogen sulfide formation by the bacteria cells or other bacteria cells.

In another embodiment, the present disclosure concerns a polynucleotide comprising (i) a DVU2956 sigma 54-dependent enhancer-binding protein (EBP) regulatory sequence operably linked to (ii) a nucleotide sequence, wherein the regulatory sequence and the nucleotide sequence are heterologous to each other, optionally wherein the regulatory sequence includes a promoter sequence. The present disclosure also concerns a cell (e.g., bacterial cell) comprising such a polynucleotide, optionally wherein the nucleotide sequence is capable of being expressed by the cell.

BRIEF DESCRIPTION OF THE DRAWINGS AND SEQUENCES

FIG. 1: Upregulation of DVU2956 (SEQ ID NO:2), DVU2960 (SEQ ID NO:4), DVU2962 (SEQ ID NO:8) and DVU2964 (SEQ ID NO:10) proteins inhibits *D. vulgaris* biofilm formation, and DVU2956 protein (SEQ ID NO:2) upregulation inhibits *D. desulfuricans* biofilm formation. Error bars indicate one standard deviation. Refer to Example 2.

Figure 2:
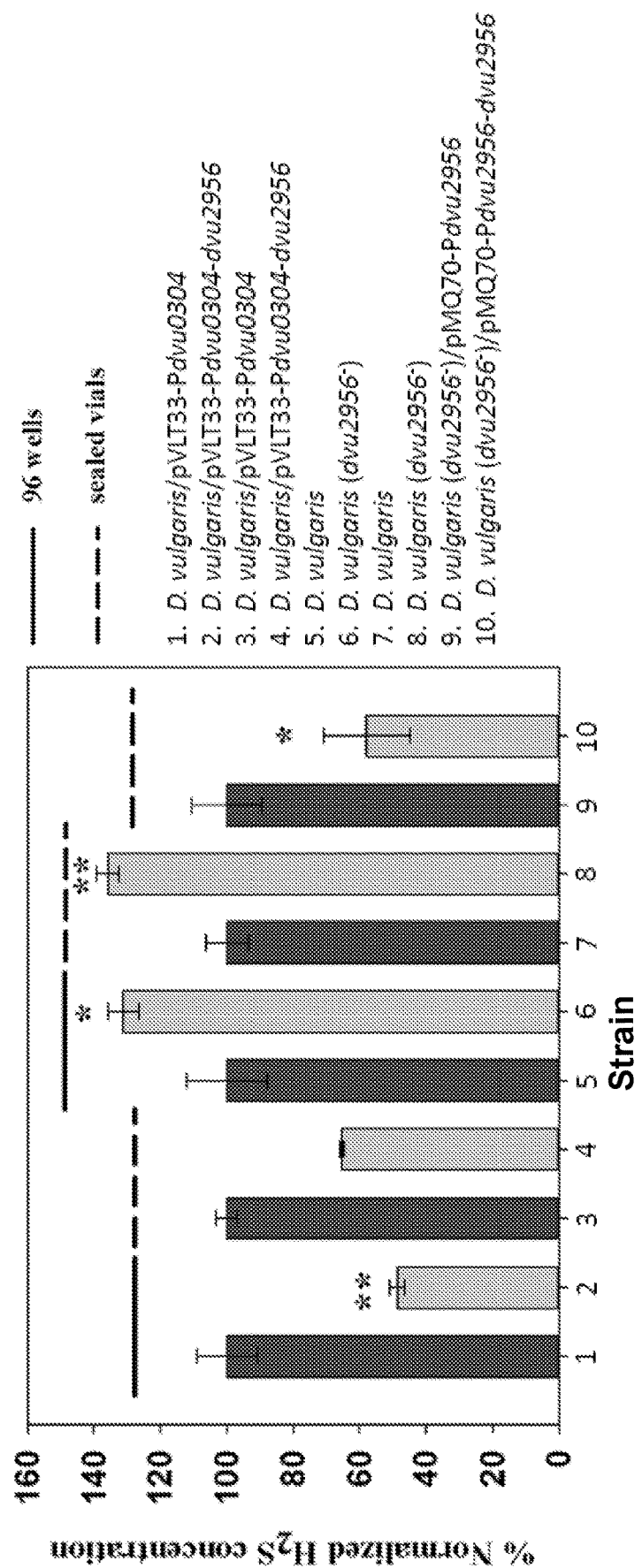

FIG. 2: Upregulation of DVU2956 protein (SEQ ID NO:2) inhibits $H_2S$ formation by *D. vulgaris* biofilm cells. Normalized $H_2S$ production (concentration [ppm]/$OD_{620\ nm}$) is respectively shown relative to negative control *D. vulgaris*/pVLT33-Pdvu0304 (for *D. vulgaris*/ pVLT33-Pdvu0304-dvu2956), negative control wild type *D. vulgaris* (for *D. vulgaris* (dvu2956⁻)), and negative control *D. vulgaris* (dvu2956⁻)/pMQ70-Pdvu2956 (for *D. vulgaris* (dvu2956⁻)/pMQ70-Pdvu2956-dvu2956). Data collected from the 96-well plate and sealed vial protocols are indicated by straight lines and dashed lines, respectively. The symbols * (P<0.05) and ** (P<0.01) indicate significant differences, per one-way ANOVA analysis, between a test and its respective control. Error bars indicate one standard deviation. Refer to Example 3.

Figure 3:
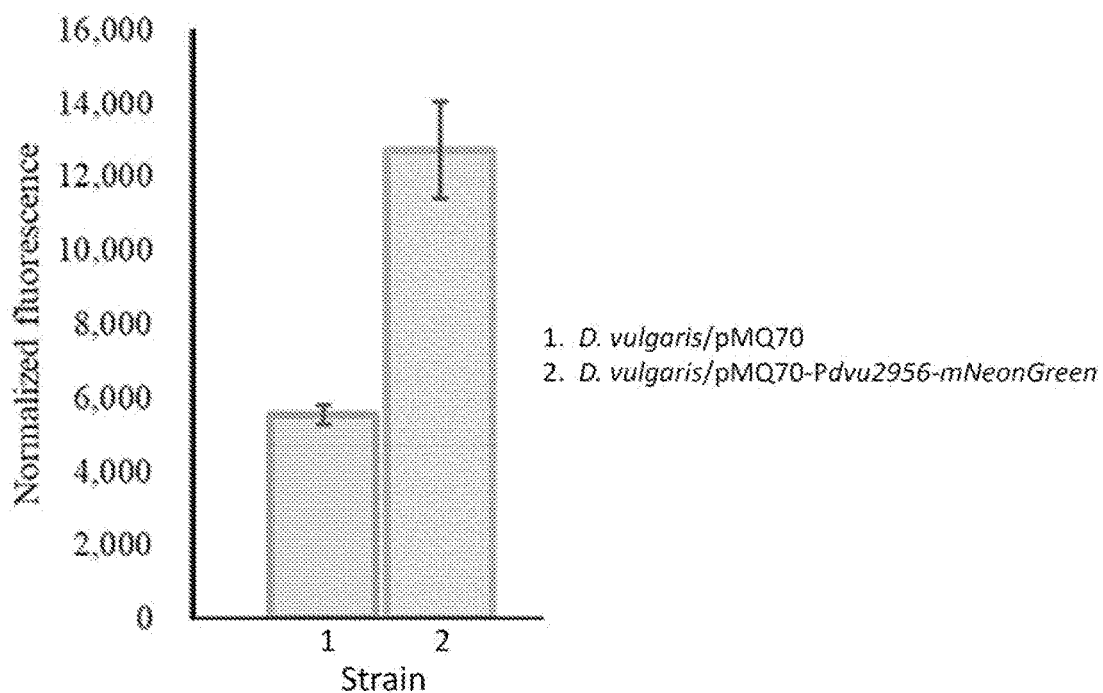

FIG. 3: Normalized fluorescence of *D. vulgaris*/pMQ70-Pdvu2956-mNeonGreen and *D. vulgaris*/pMQ70 planktonic cells at excitation of 425 nm and emission of 517 nm. Refer to Example 4.

Figure 4:
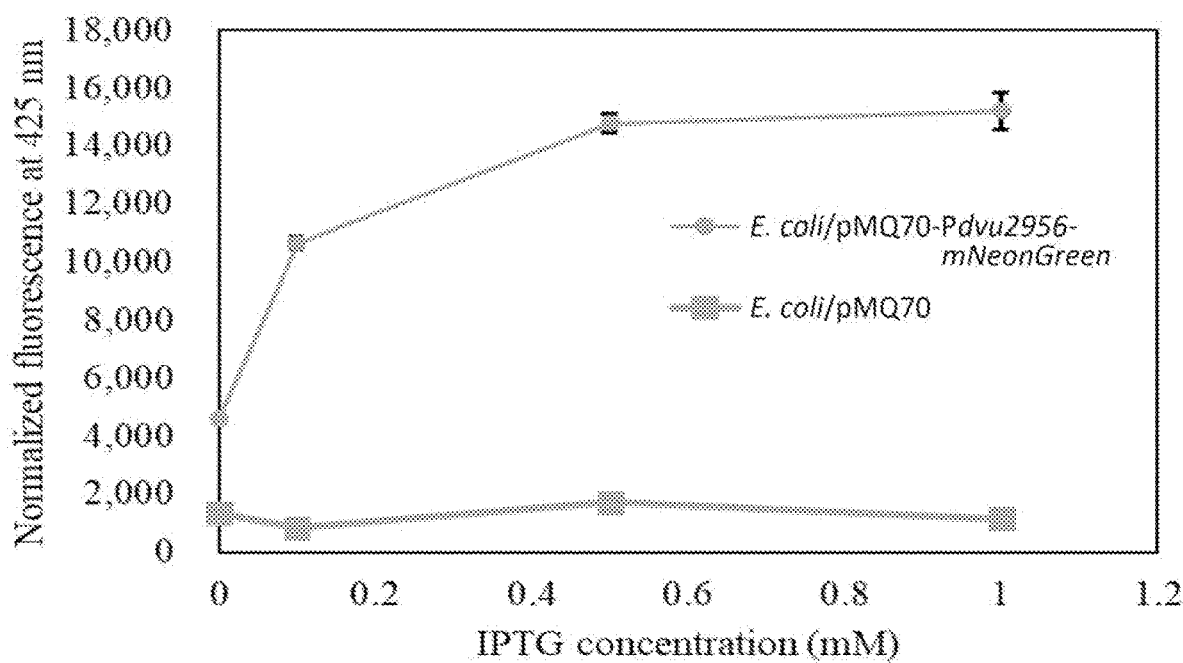

FIG. 4: Normalized fluorescence of *E. coli*/pMQ70-Pdvu2956-mNeonGreen/pET27b-dvu2956 and *E. coli*/pMQ70/pET27b-dvu2956 planktonic cells at excitation of 425 nm and emission of 517 nm, following treatment for 90 minutes with 0, 0.1, 0.5, or 1 mM IPTG. Refer to Example 4.

of sigma factors include "sigma 54" (alternatively "sigma factor 54", "$\sigma^{54}$", "sigma 54 subunit", "sigma-N" and like terms; encoded by the rpoN gene), which is a sigma factor that (i) binds a gene promoter (a "sigma 54-dependent promoter") at certain conserved nucleotide sequences typically located $-24$ (GG) and $-12$ (TGC) with respect to (i.e., 24 and 12 base pairs [bp] upstream of) the transcription start site (+1) of the gene, (ii) requires binding of a sigma 54-dependent enhancer-binding protein (EBP) at an upstream activating sequence (UAS) typically located about 100 bp or more upstream from the sigma 54-dependent promoter, and (iii) requires interaction between the EBP and sigma 54 to initiate transcription by sigma 54/RNAP complex. Sigma 54 factors have been described, for example, by Buck et al. (2000, *J. Bacteriol.* 182:4129-4136), which is incorporated herein by reference.

The terms "sigma 54-dependent enhancer-binding protein", "sigma 54-dependent EBP", "sigma 54-dependent transcriptional regulator" and the like herein refer to a bacterial protein that can bind a UAS typically (but not

TABLE 1

Summary of Nucleic Acid and Protein SEQ ID Numbers[a]

| Description | Nucleic acid SEQ ID NO. | Protein SEQ ID NO. |
|---|---|---|
| DVU2956 sigma 54-dependent EBP, *D. vulgaris* Hildenborough. | 1 | 2 (345 aa) |
| DVU2960, *D. vulgaris* Hildenborough. | 3 | 4 (474 aa) |
| DVU2961, *D. vulgaris* Hildenborough. | 5 | 6 (115 aa) |
| DVU2962, *D. vulgaris* Hildenborough. | 7 | 8 (577 aa) |
| DVU2964, D. vulgaris Hildenborough. | 9 | 10 (219 aa) |
| dvu2956 gene regulatory sequence, *D. vulgaris* Hildenborough comprising promoter and 5'-UTR sequences. | 12 | |
| dvu2956 gene promoter sequence (Pdvu2956), *D. vulgaris* Hildenborough. | 13 | |
| dvu2956 gene 5'-UTR sequence, *D. vulgaris* Hildenborough. | 14 | |
| Synthetic ribosome binding site (sRBS). | 15 | |
| Monomeric yellow-green fluorescent protein (mNeonGreen ™, GenBank ® Accession No. KC295282), codon-optimized. | 16 | |
| Pdvu2956-5' UTR-sRBS-mNeonGreen ™ cassette. | 17 | |
| Conserved motif GAFTGA of sigma 54 interaction domain of DVU2956 protein, *D. vulgaris* Hildenborough. | | 18 (6 aa) |
| Helix-turn-helix (HTH) domain of DNA-binding domain of DVU2956 protein, *D. vulgaris* Hildenborough. | | 19 (41 aa) |
| Motif within HTH domain of DVU2956 protein, *D.vulgaris* Hildenborough. | | 20 (9 aa) |
| Upstream activating sequence (UAS) consensus sequence. | 21 | |

[a]SEQ ID NO: 11 is intentionally not included in this table and merely serves as a placeholder.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The terms "sigma factor" (σ factor), "sigma subunit", "specificity factor" and the like herein refer to bacterial proteins that serve as transcription initiation factors enabling specific binding of RNA polymerase (RNAP) to a gene promoter. Sigma factors have been described, for example, by Feklistov et al. (2014, *Annu. Rev. Microbiol.* 68:357-376), which is incorporated herein by reference. Examples always) located about 100 bp or more upstream from a sigma 54-dependent promoter and activate transcriptional initiation by a sigma 54/RNAP complex that is bound to the sigma 54-dependent promoter. While a sigma 54-dependent EBP minimally requires a central ATPase (AAA+) domain that orchestrates ATP hydrolysis, EBP oligomerization and binding to sigma 54 ("sigma 54 interaction domain" herein), it typically also has a C-terminal DNA-binding domain for binding UAS and optionally also has an N-terminal regulatory domain. Sigma 54-dependent EBPs have been described, for example, by Bush et al. (2012, *Microbiol. Mol. Biol. Rev.* 76:497-529) and Kazakov et al. (2015, *BMC Genomics* 16:919), which are incorporated herein by reference.

Examples of sigma 54-dependent EBPs include "DVU2956 sigma 54-dependent EBP" (or "DVU2956 protein" and other like terms). While having a sigma 54 interaction domain, a DVU2956 sigma 54-dependent EBP herein also has a C-terminal DNA-binding domain, but lacks an N-terminal regulatory domain. In addition to the above features, the sigma 54 interaction domain of a DVU2956 sigma 54-dependent EBP typically comprises conserved motif GAFTGA (SEQ ID NO:18) and is about 150-200 (e.g. 160-170) amino acid residues in length. The DNA-binding domain of this EBP typically comprises a helix-turn-helix (HTH) domain comprising a sequence that is at least 90%, 91%, 92%, 93%, 94%, 95%, 96%, 97%, 98%, 99%, or 100% identical to SEQ ID NO:19 with motif KGEAARLLG (SEQ ID NO:20), and binds UAS with a consensus sequence of GCGGNNNNNNNNNGNCNN (SEQ ID NO:21). Such a UAS typically (but not always) is located about 100 bp or more upstream from a sigma 54-dependent promoter. DVU2956 sigma 54-dependent EBPs have been described, for example, by Kazakov et al. (2015).

The terms "biofilm", "bacterial biofilm", "surface-attached community of bacteria" and the like herein refer to a collective/assemblage/population of one or more types of bacteria cells associated with a surface. The cells in a biofilm usually are comprised within a matrix/scaffold of protein and extracellular polymeric substance(s) (EPS) such as polysaccharide material. A biofilm matrix can also comprise noncellular materials such as mineral crystals, corrosion particles, clay or silt particles, and/or other components, a biofilm of sulfate-reducing bacteria herein can, in some aspects, contain elemental sulfur and/or metal sulfide (e.g., FeS, CuS, NiS, ZnS, $TiS_2$, $MoS_2$, $Cr_2S_3$). Absent any change in protein expression as presently disclosed and/or some other treatment that alters bacterial cell physiology and/or non-cellular material in the biofilm, a bacterial biofilm typically is resistant to removal by otherwise gentle or moderate means (e.g., mild rinsing with an aqueous composition [mild fluid shear] or application of a mild agent). Biofilms typically adhere to surfaces submerged in, or subjected to, aquatic environments. Biofilms have been described, for example, by Davey and O'Toole (2000, *Microbiol. Mol. Biol. Rev.* 64:847-867), Donlan (2002, *Emerg. Infect. Dis.* 8:881-890), Satpathy et al. (2016, *Biocatal. Agric. Biotechnol.* 7:56-66), and Beech and Cheung (1995, *Int. Biodeter. Biodegr.* 35:59-72), which are incorporated herein by reference.

The term "planktonic cells" and like terms herein refer to bacteria cells floating as single cells in a liquid medium. As opposed to biofilm cells, planktonic cells typically live freely and are not associated with other cells in a matrix. A single type of bacteria can exist either in a planktonic or biofilm state, depending on environmental cues and/or gene expression, for example.

The terms biofilm "dispersal", "dispersion" and the like herein refer to the detachment of cells from a biofilm; such detached cells typically then exist in a planktonic state. Biofilm dispersal herein is active dispersal, which is driven in response to the protein upregulation introduced by the presently disclosed method. While the mechanism of dispersal herein is active, passive dispersal (e.g., via abrasion or liquid shear) can be applied, if desired, along with active dispersal.

The terms "sulfate-reducing bacteria" (SRB), "sulfide-producing bacteria", and the like herein refer to bacteria that can obtain energy by oxidizing organic compounds or molecular hydrogen while reducing sulfate ($SO_4^{2-}$) and/or other terminal sulfur-containing electron acceptors (e.g., inorganic sulfur compounds such as sulfite [$SO_3^{2-}$], dithionite [$S_2O_4^{2-}$], thiosulfate [$S_2O_3^{2-}$], trithionate [$S_3O_6^{2-}$], tetrathionate [$S_4O_6^{2-}$], elemental sulfur [$S_8$], and polysulfides [$S_n^{2-}$]) to hydrogen sulfide ($H_2S$). In general, reference to SRB herein is not intended to refer to sulfate-reducing archaea. Sulfate-reducing bacteria have been described, for example, by Muyzer and Stams (2008, *Nature Reviews Microbiology* 6:441-454), Youssef et al. (2009, *Adv. Appl. Microbiol.* 66:141-251), and Hamilton (1985, *Ann. Rev. Microbiol.* 39:195-217), which are incorporated herein by reference. Any reference herein to SRB can likewise be with respect to "sulfide-producing bacteria".

The terms "compound", "small molecule", "small-molecule compound" and the like in some aspects herein refer to a low molecular weight (e.g., <1000, 900, 800, 700, 600, 500 daltons) compound. Such a compound, for example, can be organic and/or of a size on the order of about 0.8-1.2 nm (e.g., about 1 nm).

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or combinations thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may further include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences, such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into a host organism by gene transfer. A foreign/heterologous gene herein can be (i) a native gene that is inserted into a different organism with respect to where the native gene was derived, (ii) a native gene introduced into a new location within the native host, or (iii) a chimeric gene. Polynucleotide sequences in certain embodiments disclosed herein are heterologous. A "transgene" is a gene that has been introduced into the genome by a gene delivery procedure (e.g., transformation), and therefore typically is heterologous. A "codon-optimized" open reading frame has its frequency of codon usage designed to mimic the frequency of preferred codon usage of a host cell.

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

The terms "polypeptide", "peptide", "protein" and the like herein refer to a chain of amino acid residues, usually having a defined sequence. Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

A "regulatory sequence" as used herein refers to a (i) nucleotide sequence located upstream of a gene's transcription start site (e.g., promoter), (ii) 5' untranslated region, (iii) intron, or (iv) 3' non-coding region, and may influence the transcription, processing or stability, and/or translation of an RNA sequence transcribed from the gene. Regulatory sequences herein include promoters, enhancers, silencers, 5' untranslated leader sequences, introns, polyadenylation recognition sequences, RNA processing sites, effector binding sites, stem-loop structures, and other elements involved in regulation of gene expression (from transcription through to translation). One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

An "inducible promoter" as used herein refers to a promoter capable of controlling the transcription of RNA from a gene under certain specific conditions (i.e., by the presence or absence of biotic or abiotic factors). These types of promoters typically have no, or very low, activity under conditions in which inducing conditions are not present.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are exemplified in Sambrook J, Fritsch E F and Maniatis T, *Molecular Cloning:*
*A Laboratory Manual,* 2nd ed., Cold Spring Harbor Laboratory: Cold Spring Harbor, NY (1989), which is incorporated herein by reference, particularly Chapter 11 and Table 11.1.

The terms "upstream" and "downstream" as used herein with respect to polynucleotides refer to "5' of" and "3' of", respectively.

The term "cassette" as used herein refers to a promoter operably linked to a DNA sequence encoding a protein-coding RNA or non-protein-coding RNA. A cassette may optionally be operably linked to (further comprise) a 3' non-coding sequence. Herein, a cassette as it is comprised in a plasmid construct can optionally be denoted as shown with the following example: with construct pVLT33-Pdvu0304-dvu2956, "pVLT33" refers to the plasmid backbone of the construct, "Pdvu0304" refers to the promoter, and "dvu2956" refers the nucleotide sequence (here, encoding protein DVU2956) targeted for transcription by the promoter. In some aspects, a cassette can refer to a promoter plus transcribed sequence (typically an ORF) as, for example, promoter::transcribed sequence (e.g., the foregoing example can be referred to as Pdvu0304::dvu2956).

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be upregulated or downregulated in certain embodiments.

The term "operably linked" ("operatively linked") as used herein refers to the association of two or more nucleic acid sequences such that the function of one is affected by the other. For example, a regulatory sequence (e.g., promoter) is operably linked with a coding sequence when it is capable of affecting the expression of that coding sequence. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that (i) replicates autonomously in the organism/cell, (ii) integrates into the genome of the organism/cell, or (iii) exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: (i) *Computational Molecular Biology* (Lesk, A. M., Ed.) Oxford University: NY (1988); (ii) *Biocomputing: Informatics and Genome Projects* (Smith, D. W., Ed.) Academic: NY (1993); (iii) *Computer Analysis of Sequence Data, Part I* (Griffin, A. M., and Griffin, H. G., Eds.) Humana: NJ (1994); (iv) *Sequence Analysis in Molecular Biology* (von Heinje, G., Ed.) Academic (1987); and (v) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, WI), for example. Multiple alignment of sequences can be performed, for example, using the Clustal method of alignment which encompasses several varieties of the algorithm including the Clustal V method of alignment (described by Higgins and Sharp, CAB/OS. 5:151-153 (1989); Higgins, D. G. et al., *Comput. Appl. Biosci.*, 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, CAB/OS. 5:151-153 (1989); Higgins, D. G. et al., *Comput. Appl. Biosci.* 8:189-191(1992); Thompson, J. D. et al, *Nucleic Acids Research*, 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with a sequence disclosed herein. A variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "control cell", "suitable control cell" and the like herein can be referenced with respect to a cell in which a particular modification (e.g., over-expression of a polynucleotide, down-regulation of a polynucleotide) has been made (i.e., an "experimental cell"). A control cell can be any cell that does not have or does not express the particular modification of the experimental cell. Thus, a control cell can be an untransformed wild type cell or can be genetically transformed but does not express the genetic transformation. For example, a control cell can be a direct parent of the experimental cell, which direct parent cell does not have the particular modification of the experimental cell. Alternatively, a control cell can be a parent of the experimental cell that is removed by one or more generations. Alternatively still, a control cell can be a sibling of the experimental cell, which sibling does not comprise the particular modification that is present in the experimental cell.

The term "isolated" means a composition (or process) in a form or environment that does not occur in nature. Non-limiting examples of isolated compositions include (1) any non-naturally occurring composition (e.g., a polypeptide, polynucleotide, or cell herein), (2) any composition including, but not limited to, any cell, polypeptide, polynucleotide, cofactor, or carbohydrate/saccharide that is at least partially removed from one or more of, or all of, the naturally occurring constituents with which it is associated in nature; (3) any composition modified by the hand of man relative to that composition found in nature; or (4) any composition modified by increasing or decreasing the amount of the composition relative to other components with which it is naturally associated. It is believed that embodiments, compositions and methods disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

Embodiments of the present disclosure concern a method of controlling bacteria cells. This method comprises upregulating expression of a DVU2956 sigma 54-dependent enhancer-binding protein (EBP) in the bacteria cells, thereby (i) dispersing a biofilm of the cells or reducing biofilm formation by the cells, and/or (ii) reducing hydrogen sulfide formation by the cells. Thus, the term "controlling" as used herein is generally intended to refer to inhibiting/reducing bacterial biofilm formation and/or maintenance, and/or reducing bacterial hydrogen sulfide formation.

Bacteria cells controlled by a method herein can be sulfate-reducing bacteria (SRB) cells, for example. SRB cells in some aspects include those of the taxonomic order Desulfovibrionales, Desulfobacterales, Syntrophobacterales, Nitrospirales, Clostridiales, Selenomonadales, Thermodesulfobacteriales, Desulfurellales, or Thermoanaerobacterales. Examples of Desulfovibrionales genera (and species) herein include *Desulfovibrio* (e.g., *D. vulgaris, D. sulfuricans, D. termitidis, D. gigas, D. aminophilus, D. africanus, D. putealis, D. cuneatus, D. mexicanus, D. magneticus, D. piger, D. alaskensis, D. salexigens, D. ferrophilus, D. senezii, D. fairfieldensis*), *Desulfomicrobium* (e.g., *D. escambiense, D. apsheronum, D. baculatum, D. norvegicum, D. orale, D. macestii*), *Desulfohalobium* (e.g., *D. retbaense, D. utahense*), and *Lawsonia* (e.g., *L. intracellularis*). Examples of Desulfobacterales genera (and species) herein include *Desulfobacter* (e.g., *D. postgatei*), *Desulfobulbus, Desulfobacula, Desulfotignum* (e.g., *D. toluenicum*), *Desulfobacterium* (e.g., *D. cetonicum*), and *Desulfococcus* (e.g., *D. multivorans*). Examples of Nitrospirales genera (and species) herein include *Nitrospira* (e.g., *N. moscoviensis, N. marina*). Examples of Syntrophobacterales genera (and species) herein include *Syntrophobacter* (e.g., *S. fumaroxidans*). Examples of Clostridiales genera (and species) herein include *Desulfotomaculum* (e.g., *D. australicum*). Examples of Thermodesulfobacteriales genera (and species) herein include *Thermodesulfobacterium* (e.g., *T. commune*) and *Thermodesulfatator* (e.g., *T. autotrophicus*). Yet, in some aspects, SRB cells can be those of *Desulfatitalea tepidiphila, Desulfosporosinus lacus, Thermodesulfovibrio aggregans*, or *Desulfotalea psychrophila*. Other examples of SRB of the present disclosure include any of those disclosed in Muyzer and Stams (2008, *Nature Reviews Microbiology* 6:441-454), which is incorporated herein by reference.

In some aspects, bacteria cells controlled by a method herein are those that are capable of forming a biofilm. Examples of such bacteria include any SRB cell type as disclosed herein. Other examples of bacteria of the present disclosure that are capable of forming a biofilm include the following genera (and species): *Clostridium* (e.g., *C. acetobutylicum, C. baratii, C. bifermentans, C. botulinum, C. butyricum, C. celerecrescens, C. cellulolyticum, C. clostridioforme, C. difficile, C. drakei, C. fallax, C. ljungdahlii, C. malenominatum, C. perfringens, C. phytofermentans, C. sordelli, C. thermocellum, C. magnum, C. tetani*), *Shigella* (e.g., *S. flexneri, S. dysenteriae, S. sonnei*), *Escherichia* (e.g., *E. coli, E. albertii, E. fergusonii, E. hermannii, E. vulneris*), *Bacillus* (e.g., *B. subtilis, B. licheniformis, B. coagulans, B. cereus, B. pumilus, B. ligniniphilus, B. sphaericus, B. alvei, B. laterosporus, B. megaterium, B. anthracis*), *Pseudomonas* (e.g., *P. aeruginosa, P. putida, P. syringae, P. tolaasii, P. agarici, P. oryzihabitans, P. plecoglossicida, P. hussainii*), *Klebsiella* (e.g., *K. pneumoniae, K. planticola, K. oxytoca, K. aerogenes, K. granulomatis, K. variicola*), *Staphylococcus* (e.g., *S. aureus, S. epidermidis*), *Streptococcus* (e.g., *S. pyogenes, S. viridans, S. agalactiae, S. bovis, S. pneumoniae*), *Enterococcus, Neisseria* (*N. gonorrhoeae, N. meningitidis*), *Propionibacterium* (e.g., *P. acnes*), *Corynebacterium* (e.g., *C. diphtheriae*), *Listeria* (e.g., *L. monocytogenes*), *Enterobacter, Enterococcus, Salmonella* (e.g., *S. typhimurium, S. enterica*), *Campylobacter* (e.g., *C. jejuni*). Still other examples of bacteria herein are any of those disclosed in U.S. Pat. Nos. 9,192,598 and 9,675,736, and Davey and O'Toole (2000, Microbiol. Mol. Biol. Rev. 64:847-867), Donlan (2002, *Emerg. Infect. Dis.* 8:881-890), and Satpathy et al. (2016, *Biocatal. Agric. Biotechnol.* 7:56-66), all of which references are incorporated herein by reference.

In some aspects, bacteria cells controlled by a method herein are (i) anaerobic or aerobic, and/or (ii) Gram-negative or Gram-positive. For instance, bacteria cells such as SRB cells can be anaerobic and/or Gram-negative, although SRB cells in some cases can be aerobic and/or Gram-positive. Bacteria cells in some aspects can be thermophilic, thermotolerant, or non-thermotolerant; mesophilic; and/or psychrophilic, psychrotolerant, or non-psychrotolerant. Bacteria cells in some aspects can be halophilic, halotolerant, or non-halotolerant; acidophilic, acidotolerant, or non-acidotolerant; and/or alkaliphilic, alkalitolerant, or non-alkalitolerant. Bacteria cells in some aspects can be aquatic (e.g., marine and/or fresh water) or semi-aquatic (not restricted to living in or alongside water). A population of bacteria cells herein, such those in a biofilm or a planktonic state, can be comprised of one or more (e.g., at least 2, 3, 4, 5, 6) different species of bacteria. In some aspects, a population of bacteria cells herein comprises at least about 95%, 96%, 97%, 98%, 99%, or 99.9% (of cells) of one type of bacteria species. While a biofilm here typically comprises only or mostly (e.g., >99% of biofilm cells) bacteria as its cell type, it can also comprise other types of microbial cells in some cases, such as those of archaea, protozoa, fungi/yeast, and/or algae.

A method of controlling bacteria cells herein comprises upregulating expression of a DVU2956 sigma 54-dependent enhancer-binding protein (EBP) in bacteria cells. Examples of a DVU2956 protein herein are those that are expressed by a bacteria as presently disclosed. A DVU2956 protein can be of an SRB herein in some cases, examples include a Desulfovibrionales, *Desulfovibrio, D. vulgaris, Desulfomicrobium, Desulfohalobium, Lawsonia, Desulfobacter, Desulfococcus, Nitrospira*, or *Syntrophobacter* DVU2956 protein.

It is contemplated that the amino acid sequence of a DVU2956 protein herein can comprise or consist of, for example, any of the amino acid sequences disclosed in GenBank Acc. Nos. AAS97427.1, WP_010940215.1, WP_007524656.1, WP_012612883.1, RXF76019.1, WP_035067106.1, EPR37456.1, WP_035042928.1, WP_021759108.1, WP_084630783.1, WP_027368917.1, WP_014260494.1, WP_005989720.1, WP_028576688.1, WP_043647008.1, WP_092375156.1, PKN42718.1, WP_015774434.1, WP_092188840.1, PKN09949.1, WP_034637971.1, OGR38622.1, WP_089273750.1, WP_075353577.1, OIN98835.1, WP_043635439.1, WP_015862636.1, QAZ66189.1, EKO38189.1, WP_024825447.1, OEU52209.1, OEU60302.1, RLC09126.1, RLB96743.1, RLB90370.1, KPK14763.1, PYO25948.1, PYN09170.1, PYN24203.1, RPH84916.1, PYM87057.1, WP_020876998.1, PYM29887.1, PYN47838.1, RME62715.1, PYN79803.1, OGG45084.1, KPK31454.1, RPI54032.1, WP_105329578.1, OGP61280.1, PYN88734.1, OLD39282.1, OLA97374.1, PYM70540.1, OEU44690.1, WP_013629548.1, PYN32973.1, RMF68781.1, OFV88829.1, PYN46639.1, WP_105358245.1, WP_029909485.1, PYN15987.1, WP_006522732.1, OLB08282.1, RMG02185.1, WP_129125732.1, OLD78639.1, PYM43921.1, PYM98548.1, MF47173.1, RLB82706.1, OLC13927.1, EIQ51949.1, WP_014811363.1, WP_014780627.1, KPK33783.1, OGQ36645.1, WP_000968686.1, EGJ01125.1, CSH68239.1, WP_026687822.1, RPH79962.1, WP_008686581.1, WP_035107244.1, RLB01088.1, KPJ59864.1, WP_001350708.1, WP_112058104.1, WP_053381039.1, WP_115625741.1, WP_084270987.1, WP_028455140.1, WP_080887765.1, WP_122653646.1, PYM94244.1, WP_093394811.1, RKX30710.1, PLX96612.1, and SPW53012.1, which are incorporated herein by reference. A variant of any of these amino acid sequences may be used, but should have some of (e.g., at least about 30%, 40%, 50%, 60%, 70%, 80%, 90%, or 95% of), or all of, the function (refer to above definitions) of its corresponding non-variant reference. Such a variant DVU2956 protein can comprise, or consist of, an amino acid sequence that is at least about 80%, 81%, 82%, 83%, 84%, 85%, 86%, 87%, 88%, 89%, 90%, 91%, 92%, 93% 94%, 95%, 96%, 97%, 98%, 99%, or 99.5% identical to the amino acid sequence of its corresponding non-variant reference.

In some aspects, a DVU2956 protein herein can comprise, or consist of, the amino acid sequence of SEQ ID NO:2 (a *D. vulgaris* DVU2956 protein). Alternatively, a DVU2956 protein as presently disclosed can comprise, or consist of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:2, for example. Such a variant DVU2956 protein should have some of (e.g., at least about 30%, 40%, 50%, 60%, 70%, 80%, 90%, or 95% of), or all of, the function (refer to above definitions) of the DVU2956 protein of SEQ ID NO:2.

Typically, a DVU2956 protein that is upregulated in bacteria cells herein is endogenous/native to the cells. However, upregulation by exogenously (ectopically) introducing a DVU2956 protein to bacteria cells is also envisaged. Such an exogenous DVU2956 protein can be autologous (i.e., corresponding, without amino acid variation, to the DVU2956 protein expressed endogenously by the cells) or heterologous to the cells. In some aspects, any of the foregoing DVU2956 proteins are non-native DVU2956 proteins, and thus are not 100% identical to any of the above reference sequences.

Upregulation of a DVU2956 protein in a bacteria cell herein results in an increased level of DVU2956 protein in the cell. DVU2956 protein upregulation in certain aspects can be through upregulation of a polynucleotide sequence encoding any DVU2956 protein (or variant thereof) as presently disclosed, for example. A polynucleotide sequence in some aspects comprises a nucleotide sequence that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:1 or a nucleotide sequence that encodes any of the foregoing DVU2956 proteins. Upregulation of a polynucleotide sequence encoding a DVU2956 protein can be done by one or more of a variety of methods. For example, it is contemplated that a bacteria cell herein can be treated with (contacted with, exposed to) at least one compound or agent (e.g., small molecule) that directly or indirectly induces/stimulates/activates transcription of a polynucleotide sequence encoding a DVU2956 protein; such a polynucleotide sequence typically is endogenous to the cell. As another example, a DVU2956 protein-encoding polynucleotide can be provided in multi-copy to a cell; such a polynucleotide sequence is operably linked to at least a promoter sequence that is functional in the cell. Providing a polynucleotide sequence in multi-copy can be accomplished by providing one or more copies of the polynucleotide (e.g., at least 1, 2, 3, 4, 5, 6, 7, 8, 9, 10, 15, 20, 25, or 50 copies) to a cell. As another example, a DVU2956 protein-encoding polynucleotide sequence can be upregulated through operable linkage to a constitutive promoter, strong promoter, or inducible promoter, any of which can be heterologous. Another mode of upregulating a polynucleotide sequence herein is via increasing the half-life/stability of DVU2956 protein-encoding mRNA transcripts (e.g., potentially via treatment of cells with at least one compound or agent having this effect).

Other modes of upregulating expression of a DVU2956 protein in bacteria herein include increasing translation of mRNA encoding DVU2956 protein, and/or increasing the half-life/stability of DVU2956 protein. Another mode of upregulating DVU2956 protein herein involves enhancing a function/activity of the protein, thereby enhancing the ability of DVU2956 protein to allow sigma 54-dependent transcription. It is contemplated that one or more of these additional modes of upregulation can be effected by treating bacteria with at least one compound or agent (e.g., small molecule).

Upregulation of a DVU2956 protein in a bacteria cell herein can optionally be considered with respect to a suitable control cell. For example, the increased level of a DVU2956 protein (or an RNA transcript encoding it) in a cell can be characterized to be about, or at least about, 25%, 50%, 100%, 150%, 200%, 250%, 500%, 1000%, 1500%, 2000%, 2500%, 3000%, 4000%, 5000%, or 10000% above the expression of the DVU2956 protein (or an RNA transcript encoding it) in a suitable control cell. An example of a suitable control cell is a cell as it existed before it was modified to have upregulated DVU2956 protein expression. An example of a control bacteria cell for the purposes of this disclosure is one that is in a biofilm. Thus, for example, DVU2956 protein upregulation as determined in a cell that has been dispersed from a biofilm following the disclosed method can be as compared to DVU2956 protein expression as it existed in the cell when it was in the biofilm.

DVU2956 protein expression in bacteria cells of a biofilm, prior to upregulation, is repressed by the cells in some aspects. Since repression herein is contemplated to generally be due to, at least in part, repressed transcription of a polynucleotide encoding DVU2956 protein, repression can also be determined by measuring the level of DVU2956 protein-encoding mRNA transcripts. Repression can mean, for example, that there is no DVU2956 protein expressed by the cells, or its level is below detection limits. In some aspects, repression of DVU2956 protein expression (or of its encoding mRNA transcripts) in bacteria cells of a biofilm can mean that the expression is about, or at least about, 1-, 1.5-, 2-, 2.5-, 5-, 10-, 15-, 20-, 25-, 30-, 40-, 50-, or 100-fold less than the DVU2956 protein expression (or of its encoding mRNA transcripts) of cells that have been dispersed from a biofilm (e.g., are now planktonic) following the disclosed method.

A comparison of DVU2956 protein (or RNA) expression between biofilm cells and cells that have dispersed from the biofilm following DVU2956 protein upregulation herein can optionally be made at about, or at least about, 0, 1, 2, 4, 6, 8, 10, 12, 15, 18, 21, or 24 hours following dispersal. Protein expression comparisons herein can be made using any suitable protein expression analysis such as spectrometry (e.g., high-performance liquid chromatography [HPLC], liquid chromatography-mass spectrometry [LC/MS]) or an antibody-dependent method (e.g., enzyme-linked immunosorbent assay [ELISA], western blotting, immunoprecipitation). Expression comparisons as determined at the transcriptional level herein can be made using a transcriptional expression analysis such as northern blotting, quantitative reverse transcription polymerase chain reaction (qRT-PCR), microarray analysis, serial analysis of gene expression (SAGE), or comparative transcriptomic analysis (RNA-Seq, also referred to as whole transcriptome shotgun sequencing).

In some aspects, DVU2956 protein upregulation is done to inhibit/reduce biofilm formation by bacteria (e.g., prevent planktonic bacteria cells from forming a biofilm), while in some aspects DVU2956 protein upregulation is done to inhibit/reduce biofilm maintenance (e.g., cause the dispersal of bacteria cells from the biofilm). Still, in some aspects, DVU2956 protein upregulation is done to inhibit/reduce sulfide (e.g., hydrogen sulfide) formation by bacteria cells, this aspect can optionally also characterize dispersing biofilm cells (typically SRB) using the disclosed method.

Dispersal of biofilms herein typically refers to, at a minimum, dispersing live bacteria cells from a biofilm. In some aspects, biofilm dispersal comprises only dispersal of live bacteria cells, or dispersal of live cells and other biofilm components (e.g., dead cells, one or more biofilm matrix components). The percentage of live bacteria cells in a biofilm that disperse upon upregulating a DVU2956 protein herein can be about, or at least about, 10%, 20%, 30%, 40%, 50%, 60%, 70%, 80%, 90%, 95%, 99%, or 100%. A bacteria cell herein that has been dispersed from a biofilm typically is planktonic, and/or dies in some aspects. An entire biofilm or most of it (e.g., over 90%, 95% or 99% by weight), including both its live and non-living components, can be dispersed in some embodiments. Biofilm dispersal can be measured following the disclosure of Guilhen et al. (2017, Mol. Microbiol. 105:188-210, incorporated herein by reference), for example. While no passive dispersal action is necessary for achieving dispersal in typical embodiments, such an action can be combined with the presently disclosed method if desired.

A reduction of biofilm formation by bacteria herein resulting from upregulating a DVU2956 protein can be by about, or at least about, 50%, 60%, 70%, 80%, 90%, 95%, 99%, or 100%, for example, as compared to the amount or rate of biofilm formation that would have occurred if DVU2956 protein upregulation was not performed. In some aspects, upregulating a DVU2956 protein herein can reduce (e.g., by over 80%, 90%, or 95%) or completely block the rate of growth/spreading of an established bacterial biofilm as compared to the rate of growth/spreading that would have occurred if DVU2956 protein upregulation was not performed.

A reduction of hydrogen sulfide ($H_2S$) formation by bacteria cells herein (typically SRB) resulting from upregulating a DVU2956 protein can be by about, or at least about, 10%, 20%, 30%, 40%, 50%, 60%, 70%, 80%, 90%, 95%, 99%, or 100%, for example, as compared to the hydrogen sulfide formation that would have occurred if DVU2956 protein upregulation was not performed. Hydrogen sulfide can be measured following the disclosure in the below Examples or as disclosed in Rabinowitz (1978, *Methods Enzymol.* 53:275-277, incorporated herein by reference), for example. Since aspects of the disclosed method are drawn to controlling hydrogen sulfide formation, these aspects can alternatively be characterized as a method of controlling souring such as that occurring in some industrial settings (see below), and thus also as a method of controlling corrosion brought on by hydrogen sulfide. Based on this latter point, such a method can optionally be characterized as a method of controlling metal sulfide production (such as that formed during corrosion of metal), examples of which include iron sulfide (FeS), copper sulfide (CuS), nickel sulfide (NiS), zinc sulfide (ZnS), tin sulfide ($TiS_2$), molybdenum sulfide ($MoS_2$) and chromium sulfide ($Cr_2S_3$).

Upregulation of a DVU2956 protein in bacteria cells herein can be performed for about, or at least about, 3, 6, 8, 10, 12, 15, 18, 21, 24, 30, 36, 42, 48, 60, 72, 84, or 96 hours, for example, to effectively control the bacterial cells as disclosed herein. The temperature in which bacteria cells herein are induced for DVU2956 protein upregulation can be about, at least about, or up to about, -1, 0, 1, 2, 3, 4, 5, 10, 15, 20, 25, 30, 35, 40, 45, 50, 60, 70, 75, 80, 85, 15-40, 15-70, 15-85, or 70-85° C., for example.

Upregulation of a DVU2956 protein in bacteria cells herein can be performed by treating the cells to upregulate expression of the DVU2956 protein. For example, such upregulation can be induced by treating (or exposing or contacting) bacteria cells herein with at least one compound or agent (e.g., small molecule). Examples of a compound for upregulating DVU2956 protein expression herein are those that can induce transcriptional activation of a dvu2956 promoter as identified by a method of the present disclosure (see below). In some aspects, such as transcriptional activation of a dvu2956 promoter, a compound acts directly by interacting with a factor that itself is directly involved in orchestrating regulation of DVU2956 protein expression (e.g., a transcription factor or polymerase that regulates a dvu2956 promoter), while in other aspects the compound acts indirectly on factors that are mechanistically upstream of a factor that directly regulates DVU2956 protein expression.

A compound for upregulating DVU2956 protein expression in some aspects can be comprised in an aqueous composition or non-aqueous composition, typically depending on the nature of the compound itself (e.g., hydrophilic or hydrophobic) and/or the environment in which the bacteria are treated. Such a composition can be a solution or a dispersion/emulsion, for example. The solvent of a liquid composition comprising a compound herein can comprise about, at least about, or less than about, 0, 10, 20, 30, 40, 50, 60, 70, 80, 90, or 100 wt % water, for example. In some aspects, the composition can be formulated as a liquid, lotion, cream, spray, gel, ointment, washing powder, or cleaning agent such as a cleaning solution, cleaning liquid, cleaning lotion, cleaning cream, cleaning spray, cleaning gel and the like. In some aspects, a compound for upregulating DVU2956 protein expression can be present in a composition (formulation) that further comprises one or more of a surfactant/detergent, solubilizing agent (typically for solubilizing the compound), buffer, salt, viscosity/rheology modifier, lubricant, or metal chelator, and/or any of these or other ingredients or formulations as disclosed in Worthington et al. (2012, *Org. Biomol. Chem.* 10:7457-7474), Zain et al. (2018, *Int. J. Corrosion* vol. 2018, pp. 1-7, article ID 3567569), Cheung and Beech (1996, *Biofouling* 9:231-249), or U.S. Patent Appl. Publ. Nos. 2013/0029884, 2005/0238729, 2010/0298275, 2013/0052250, 2015/009891, 2016/0152495, or 2016/0152495, or U.S. Pat. Nos. 4,552,591, 4,925,582, 6,478,972, 6,514,458, 6,395,189, 7,927,496, or 8784659, which are incorporated herein by reference. It is contemplated that upregulation of a DVU2956 protein in bacteria cells, such as by treatment with a compound, generally is not biocidal. For example, all of, or at least 95% or 99% of, bacteria cells are not killed when induced to upregulate DVU2956 protein expression. A compound or treatment herein that upregulates DVU2956 protein expression generally is not biocidal against bacteria such as SRB. For example, a compound that upregulates DVU2956 protein expression typically is not one as disclosed in any of the foregoing references. In some aspects, a compound for upregulating DVU2956 protein expression herein, while generally not biocidal itself, can be used in conjunction with a biocidal compound such as disclosed in any of the foregoing references.

In some aspects, bacteria cells that are targeted for upregulating DVU2956 protein expression can be on, or adjacent to, a surface, such as would be the case if the cells are in a biofilm. A surface can be abiotic, inert, and/or biotic (of life or derived from life), for example. An abiotic or inert surface can comprise a metal (e.g., iron, copper, nickel, zinc, titanium, molybdenum, chromium), for example, and optionally be a metal alloy (e.g., steel, stainless steel). An abiotic or inert surface in some other aspects can comprise plastic, rubber, porcelain/ceramic, silica/glass, and/or mineral material (e.g., stone/rock/concrete).

An abiotic or inert surface in some aspects can be of a device/component/equipment and/or system/process of an industrial setting. Examples of industrial settings herein include those of an energy (e.g., fossil fuel such as petroleum), water (e.g., water treatment and/or purification, industrial water, wastewater treatment), agriculture (e.g., grain, fruits/vegetables, fishing, aquaculture, dairy, animal farming, timber, plants), chemical (e.g., pharmaceutical, chemical processing), food processing/manufacturing, mining, or transportation (e.g., fresh water and/or maritime shipping, train or truck container) industry.

An abiotic or inert surface in some aspects can be of a device/component/equipment and/or system/process of a water treatment, water storage, and/or other water-bearing system (e.g., piping/conduits, heat exchangers, condensers, filters/filtration systems, storage tanks, water cooling towers, pasteurizers, boilers). An abiotic or inert surface in some aspects can be of a device/component/equipment and/or system/process of a fossil fuel (e.g., oil/petroleum or natural gas) extraction, storage, delivery, or processing/refining operation (e.g., oil drilling pipes, oil pipelines, oil storage tanks, gas drilling pipes, gas pipelines, offshore rig, wellbore, wellhead, shipping containers, oil well/down hole). Such an extraction (recovery) operation can be based on land or offshore. An abiotic or inert surface in some aspects can be of a ship (e.g., hull, ballast tank).

An abiotic or inert surface in some aspects can be of a device/component/equipment and/or system/process of a medical/dental/healthcare setting (e.g., hospital, clinic, examination room, nursing home), food service setting (e.g., restaurant, commissary kitchen, cafeteria), retail setting (e.g., grocery, soft drink machine/dispenser), hospitality/travel setting (e.g., hotel/motel), sports/recreational setting (e.g., gym, exercise equipment, locker room, aquatics/tubs, spa), or office/home setting (e.g., bathroom, tub/shower, kitchen, air vents, appliances [e.g., fridge, freezer], sprinkler system). Examples of medical devices include contact lenses, intravenous catheters and connectors, endotracheal tubes, intrauterine devices, mechanical heart valves, pacemakers, peritoneal dialysis catheters, prosthetic joints, tympanostomy tubes, urinary catheters, voice prostheses, and instruments. Another abiotic or inert surface herein can be of a water (optionally potable water) installation (e.g., water storage tank, water heater) or where there is standing or condensed water (e.g., as sometimes found in an air/ventilation duct).

In some aspects, bacteria cells that are targeted for upregulating DVU2956 protein expression can be comprised in any of the foregoing settings (e.g., industrial, medical/dental/healthcare, food service, retail, hospitality/travel, sports/recreational, office/home) in a planktonic state. Biofilm formation is inhibited or reduced in these settings by following the disclosed upregulation method.

In some aspects, bacteria cells that are targeted for upregulating DVU2956 protein expression can be comprised on a biotic surface (e.g., biofilm) or otherwise in a biotic setting (e.g., planktonic state). A biotic surface or setting can optionally be associated with any of the foregoing settings, such as an industrial setting (e.g., petroleum, wood/pulp processing, animal meat processing, food processing) or medical/dental/healthcare setting (e.g., teeth, skin/nails/wounds, body orifice [e.g., nasal, oral, genitourinary], gastrointestinal/alimentary canal, eye/conjunctiva, ear/ear canal, pulmonary, cardiovascular). A biotic surface or setting can optionally be associated with food (e.g., fruit/vegetable, meat/fish [e.g., frozen, cured], pre-prepared food/meal [e.g., frozen, fresh], dairy product, grain product).

Accordingly, the presently disclosed methods and compositions can be adapted for controlling bacteria in various applications, such as those associated with any of the above aspects. Just to illustrate, they can be used in various phases of oil or natural gas production, transmission, and storage, both topside and downhole, such as in aeration towers, de-aeration towers, storage tanks, injection water, production water, pigging operations, drilling muds, completion or workover fluids, stimulation fluids, packing fluids, fracturing fluids, and hydrotest fluids. As other examples, the presently disclosed methods and compositions can be used in water treatment and purification processes/systems (e.g., membranes and other system components that are susceptible to fouling); paper and pulp production; ballast water disinfection; preventing bacterial contamination of water-based fluids and systems used in cooling and/or heating processes; and preventing bacterial contamination of water-based slurry, ink and tape-joint compounds, water-based household products and personal care products, latex, paint, and coatings. As other examples, the presently disclosed methods and compositions can be used for any application, system/process, apparatus, and/or surface as disclosed in any of U.S. Patent Appl. Publ. Nos. 2013/0029884, 2005/0238729, 2010/0298275, 2016/0152495, 2013/0052250, 2015/009891, or 2016/0152495, or U.S. Pat. Nos. 4,552,591, 4,925,582, 6,478,972, 6,514,458, 6,395,189, 7,927,496, or 8784659, which are all incorporated herein by reference.

Embodiments of the present disclosure concern other methods of controlling bacteria cells. These other methods comprise upregulating expression of a DVU2960 protein, DVU2962 protein, and/or a DVU2964 protein in bacteria cells, thereby (i) dispersing a biofilm of the cells or reducing biofilm formation by the cells, and/or (ii) reducing hydrogen sulfide formation by the cells. In some aspects, a DVU2960 protein herein can comprise, or consist of, the amino acid sequence of SEQ ID NO:4. Alternatively, a DVU2960 protein herein can comprise, or consist of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:4, for example. In some aspects, a DVU2962 protein herein can comprise, or consist of, the amino acid sequence of SEQ ID NO:8. Alternatively, a DVU2962 protein herein can comprise, or consist of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:8, for example. In some aspects, a DVU2964 protein herein can comprise, or consist of, the amino acid sequence of SEQ ID NO:10. Alternatively, a DVU2964 protein herein can comprise, or consist of, an amino acid sequence that is at least about 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:10, for example. A variant DVU2960, DVU2962, or DVU2964 protein should have some of (e.g., at least about 30%, 40%, 50%, 60%, 70%, 80%, 90%, or 95% of), or all of, the function of its respective non-variant DVU2960, DVU2962, or DVU2964 protein. It is contemplated that any embodiment disclosed herein of upregulating expression of a DVU2956 protein to control bacterial cell biofilm formation and/or maintenance, as reasonably appropriate, can alternatively employ upregulating expression of a DVU2960, DVU2962, and/or DVU2964 protein to effect such bacterial cell control. Upregulating expression of a DVU2960, DVU2962, and/or DVU2964 protein in bacteria cells herein can optionally be in addition to upregulating expression of a DVU2956 protein in the cells.

Embodiments of the present disclosure also concern a method of identifying a candidate compound for controlling bacteria cells. This method can comprise: (a) providing bacteria cells comprising a polynucleotide that comprises (i) a DVU2956 sigma 54-dependent enhancer-binding protein (EBP) regulatory nucleotide sequence operably linked to (ii) a nucleotide sequence ("reporter nucleotide sequence"); (b) contacting the bacteria cells of step (a) with at least one test compound (small molecule); and (c) determining whether expression of the nucleotide sequence by the bacteria cells of step (b) is upregulated, wherein such upregulation indicates that the test compound is a candidate compound for (i) controlling biofilm maintenance or biofilm formation by the bacteria cells or other bacteria cells, and/or (ii) reducing hydrogen sulfide formation by the bacteria cells or other bacteria cells. Such a method can optionally be characterized as a screening method. Steps (a) and (b) of a screening method herein can be performed separately or together; step (b) in-and-of-itself encompasses step (a). A candidate compound identified by a screening method herein can optionally be characterized as a compound (putative compound) for controlling bacteria as presently disclosed. Typically, a polynucleotide of a screening method herein is heterologous, in that it is heterologous with respect to the bacteria cells, and/or its DVU2956 protein regulatory sequence is heterologous to its reporter nucleotide sequence.

Bacteria cells employed in steps (a)-(c) of a screening method in some aspects can be any type of bacteria cell disclosed herein, such as above or in the below Examples. For example, the bacteria cells can be SRB (e.g., *Desulfovibrio* species), *E. coli*, or *Bacillus* cells.

A DVU2956 protein regulatory nucleotide sequence in some aspects of a screening method herein can comprise one or more regulatory sequences. For example, a regulatory sequence can comprise a promoter sequence, upstream activating sequence (and/or other transcription factor binding sequence), and/or 5'-untranslated region (5'-UTR) sequence, all of which are typically derivable from a dvu2956 gene/locus. In some aspects, a regulatory sequence herein can comprise (i) a promoter or (ii) a promoter that is operably linked to a 5'-UTR sequence. Typically, a reporter nucleotide sequence of a heterologous polynucleotide herein is operably linked downstream of a regulatory sequence. If the reporter nucleotide sequence contains an open reading frame and is intended to be expressible as a protein, a ribosome binding site (RBS, Shine-Dalgarno sequence) (native, synthetic, and/or heterologous) typically is included upstream of the start codon; a spacer sequence located between the 3'-end of an RBS and the start codon, if present, can be about 2-10 bp (e.g., 5-7 bp) long, for example. Any suitable RBS sequence can be employed, such as one disclosed herein. In some aspects, a regulatory sequence (e.g., promoter and/or 5'-UTR) is located immediately upstream of a start codon or RBS, or about, or within about, 1, 2, 3, 4, 5, 6, 7, 8, 9, 10, 1-50, 1-25, 1-20, 1-15, 1-10, or 1-5 bp upstream.

Examples of a promoter for use in a regulatory sequence herein can comprise or consist of a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% to identical to SEQ ID NO:13. Examples of a 5'-UTR for use in a regulatory sequence herein can comprise or consist of a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% to identical to SEQ ID NO:14. In aspects in which a regulatory sequence comprises both promoter and 5'-UTR sequences, such a regulatory sequence can comprise or consist of a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% to identical to SEQ ID NO:12, for example. In some aspects, a DVU2956 protein regulatory nucleotide sequence is derivable from any type of bacteria as disclosed herein. While a DVU2956 protein regulatory nucleotide sequence of a screening method herein can be heterologous to the bacteria cells used in the method (e.g., assaying an SRB regulatory sequence in a commonly used lab strain such as *E. coli*), it can be autologous to the bacteria cells in some other aspects (e.g., assaying a *D. vulgaris* regulatory sequence in a *D. vulgaris* strain).

A reporter nucleotide sequence of a heterologous polynucleotide in a screening method herein can encode a protein (i.e., comprise an open reading frame). Such a protein can optionally be characterized as a reporter protein. Increased expression of reporter protein by bacterial cells of step (b) of a screening method herein indicates upregulated expression of the reporter nucleotide sequence. Increased reporter protein expression can be discerned by detecting the reporter protein directly (e.g., using an antibody-dependent method or spectrometry method as disclosed above) and/or by detecting activity/function of the reporter protein (e.g., enzymatic activity, fluorescence). Examples of a reporter protein herein include glutathione-5-transferase (GST), horseradish peroxidase (HRP), chloramphenicol acetyltransferase (CAT), beta-galactosidase, beta-glucuronidase (GUS), luciferase, green fluorescent protein (GFP), HcRed, DsRed, cyan fluorescent protein (CFP), yellow fluorescent protein (YFP), blue fluorescent protein (BFP), and yellow-green fluorescent protein. In some aspects, a reporter nucleotide sequence of a heterologous polynucleotide does not encode a protein, in which case its upregulation can be measured by detecting RNA transcripts of the reporter nucleotide sequence (e.g., using any RNA detection method herein).

In some aspects, upregulated expression of a reporter nucleotide sequence in a screening method herein is increased expression of the nucleotide sequence by about, or at least about, 25%, 50%, 100%, 150%, 200%, 250%, 500%, 1000%, 1500%, 2000%, 2500%, 3000%, 4000%, 5000%, or 10000% above its expression by a suitable control (e.g., the bacteria cells prior to contacting them with a test compound). Increased reporter nucleotide sequence expression can be, for example, based on measuring levels of encoded protein, protein activity, and/or RNA transcripts of the reporter nucleotide sequence.

A heterologous polynucleotide of a screening method herein can optionally be characterized as a reporter or reporter construct, for example. Examples of such a reporter construct can be selected from a plasmid, cosmid, phagemid, bacterial artificial chromosome (BAC), virus/phage, or linear DNA (e.g., linear PCR product). A reporter construct in some aspects can be capable of existing transiently (i.e., not integrated into the genome) or stably (i.e., integrated into the genome) in a bacterial cell. A reporter construct in some aspects can comprise, or lack, one or more suitable marker sequences (e.g., selection or phenotype marker).

Upregulated expression of a reporter nucleotide sequence by a DVU2956 protein regulatory sequence in a screening method herein indicates that (1) a test compound is potentially able to upregulate dvu2956 gene expression in the bacteria from which the regulatory sequence was derived (or is derivable from), and/or (2) a test compound is potentially able to upregulate dvu2956 gene expression in another type of bacteria. This in turn indicates that the test compound is a candidate compound for upregulating DVU2956 protein expression, and therefore also that it is a candidate compound for (i) controlling biofilm maintenance or biofilm formation by bacteria cells, and/or (ii) reducing hydrogen sulfide formation by bacteria cells. These effects (i and ii) can be any of those as described herein regarding upregulating DVU2956 protein expression.

A screening method can further comprise one or more of following steps (d)-(f) to determine whether a candidate compound (identified in step c) is suitable for controlling bacteria:
  (d) contacting the bacteria cells or other bacteria cells comprised in a biofilm with the candidate compound identified in step (c), wherein dispersal of the biofilm indicates that the candidate compound inhibits biofilm maintenance;
  (e) contacting the bacteria cells or other bacteria cells comprised in a liquid culture with the candidate compound identified in step (c), wherein an inability of the bacteria cells or other bacteria cells to form a biofilm indicates that the candidate compound inhibits biofilm formation; and/or
  (f) contacting the bacteria cells or other bacteria cells with the candidate compound identified in step (c), wherein a reduction in $H_2S$ production by the bacteria cells or other bacteria cells indicates that the candidate compound inhibits $H_2S$ production by the bacteria cells or other bacteria cells.

Step (d) typically further comprises a step of determining or measuring biofilm dispersal by bacteria contacted with the candidate compound. The degree of dispersal can be as disclosed above. Step (e) typically further comprises a step of determining or measuring biofilm formation by bacteria contacted with the candidate compound. The degree of reduction of biofilm formation can be as disclosed above. Step (f) typically further comprises a step of determining or measuring $H_2S$ production by bacteria contacted with the candidate compound. The degree of reduction of $H_2S$ production can be as disclosed above.

In some aspects, the bacteria used in steps (a)-(c) of a screening method is the same as the bacteria from which the DVU2956 protein regulatory sequence was derived (or is derivable from), while in other aspects the bacteria used in steps (a)-(c) is the different from the bacteria from which the DVU2956 protein regulatory sequence was derived (or is derivable from). In some aspects, the bacteria used in steps (a)-(c) of a screening method is the same as the bacteria used in step(s) (d), (e), and/or (f), while in other aspects the bacteria used in steps (a)-(c) is different from the bacteria used in step(s) (d), (e), and/or (f). In some aspects, step(s) (d), (e), and/or (f) is/are conducted with the same type of bacteria from which the DVU2956 protein regulatory sequence was derived (or is derivable from). In some less typical aspects, a screening method employs a bacteria in which the bacteria's endogenous dvu2956 gene is used as the reporter polynucleotide sequence for assaying whether a candidate compound can control bacteria cells.

Test/candidate compounds of a screening method herein can optionally be formulated as described above for formulating a compound for upregulating DVU2956 protein expression in applications of controlling bacteria. Steps of contacting a test/candidate compound with bacteria cells can be performed for about, or at least about, 3, 6, 8, 10, 12, 15, 18, 21, 24, 30, 36, 42, 48, 60, 72, 84, or 96 hours, for example. The temperature in which bacteria cells in a screening method are contacted with a test/candidate compound can be about, at least about, or up to about, −1, 0, 1, 2, 3, 4, 5, 10, 15, 20, 25, 30, 35, 40, 45, 50, 60, 70, 75, 15-40, or 15-70° C., for example. Bacteria cells in a screening method herein can be grown in any media and/or conditions suitable for growing the bacteria cells (e.g., below Examples), and/or in conditions that are similar to or the same as those in which the bacteria live in the field.

A screening method in some aspects comprises screening a plurality of test compounds by following steps (a)-(c) to identify one or more candidate compounds for controlling bacteria cells. A plurality of test compounds can optionally be characterized as a library of compounds. A library herein can comprise about, or at least about, 5000, 10000, 25000, 50000, 100000, 250000, 500000, 750000, or 1000000 compounds, for example. Test compounds can be applied in a screening method individually or in combination with other test compounds; the latter approach eventually leads to screening compounds on an individual basis after identifying one or more pools of compounds that upregulate the reporter nucleotide sequence.

Embodiments of the present disclosure also concern a polynucleotide comprising (i) a DVU2956 sigma 54-dependent enhancer-binding protein (EBP) regulatory sequence operably linked to (ii) a nucleotide sequence, wherein the regulatory sequence and the nucleotide sequence are heterologous to each other, optionally wherein the regulatory sequence includes a promoter sequence. A DVU2956 protein regulatory sequence and/or nucleotide sequence of such a polynucleotide can be any of those disclosed herein (e.g., as in the above screening method or below Examples). In some alternative aspects, the regulatory sequence and the nucleotide sequence are autologous to each other.

A polynucleotide herein comprising a DVU2956 protein regulatory sequence and nucleotide sequence can be a vector or construct useful for transferring a nucleotide sequence into a cell and/or testing activity of the regulatory sequence (as above), for example. Examples of a suitable vector/construct can be selected from a plasmid, yeast artificial chromosome (YAC), cosmid, phagemid, bacterial artificial chromosome (BAC), virus/phage, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

Some aspects herein are drawn to a cell comprising a polynucleotide sequence as presently disclosed. Such a cell can be any bacterial cell as disclosed herein (e.g., *E. coli*, *Bacillus*, SRB [e.g., *Desulfovibrio* species]), for example. In some aspects, a cell can be a eukaryotic cell such as a fungus (e.g., yeast), insect, or mammalian cell. A cell can optionally be capable of using the DVU2956 protein regulatory sequence to express the nucleotide sequence of the polynucleotide. In some aspects, the polynucleotide sequence exists transiently (i.e., not integrated into the genome) or stably (i.e., integrated into the genome) in the cell.

Non-limiting examples of compositions and methods disclosed herein include:

1. A method of controlling bacteria cells, the method comprising: upregulating expression of a DVU2956 sigma 54-dependent enhancer-binding protein (EBP) in the bacteria cells, thereby (i) dispersing a biofilm of the cells or reducing biofilm formation by the cells, and/or (ii) reducing hydrogen sulfide formation by the cells.
2. The method of embodiment 1, wherein the cells are sulfate-reducing bacteria (sulfide-producing bacteria) cells.
3. The method of embodiment 2, wherein the cells are of the order Desulfovibrionales.
4. The method of embodiment 3, wherein the cells are of the genus *Desulfovibrio*.
5. The method of embodiment 1, 2, 3, or 4, wherein the DVU2956 sigma 54-dependent EBP is endogenous to the cells.
6. The method of embodiment 1, 2, 3, 4, or 5, wherein the cells are comprised within a biofilm, and the biofilm is dispersed following the upregulation step.
7. The method of embodiment 1, 2, 3, 4, 5, or 6, wherein expression of the DVU2956 sigma 54-dependent EBP prior to the upregulation step is repressed by the cells.
8. The method of embodiment 1, 2, 3, 4, 5, 6, or 7, wherein the cells are treated with at least one compound to induce the upregulated expression of the DVU2956 sigma 54-dependent EBP.
9. The method of embodiment 1, 2, 3, 4, 5, 6, 7, or 8, wherein the cells are on one or more surfaces of industrial equipment (one or more surfaces of a piece of industrial equipment) or are otherwise present in an industrial process.
10. A method of identifying a candidate compound for controlling bacteria cells, the method comprising: (a) providing bacteria cells comprising a polynucleotide that comprises (i) a DVU2956 sigma 54-dependent enhancer-binding protein (EBP) regulatory sequence operably linked to (ii) a nucleotide sequence; (b) contacting the bacteria cells of step (a) with at least one test compound; and (c) determining whether expression of the nucleotide sequence by the bacteria cells of step (b) is upregulated, wherein such upregulation indicates that the test compound is a candidate compound for (i) controlling biofilm maintenance or biofilm formation by the bacteria cells or other bacteria cells, and/or (ii) reducing hydrogen sulfide formation by the bacteria cells or other bacteria cells.
11. The method of embodiment 10, further comprising: (d) contacting the bacteria cells or other bacteria cells comprised in a biofilm with the candidate compound identified in step (c), wherein dispersal of the biofilm indicates that the candidate compound inhibits biofilm maintenance; (e) contacting the bacteria cells or other bacteria cells comprised in a liquid culture with the candidate compound identified in step (c), wherein an inability of the bacteria cells or other bacteria cells to form a biofilm indicates that the candidate compound inhibits biofilm formation; or (f) contacting the bacteria cells or other bacteria cells with the candidate compound identified in step (c), wherein a reduction in hydrogen sulfide production by the bacteria cells or other bacteria cells indicates that the candidate compound inhibits hydrogen sulfide production by the bacteria cells or other bacteria cells.
12. The method of embodiment 10 or 11, wherein the nucleotide sequence comprises a sequence that encodes a reporter protein, wherein increased expression of the reporter protein by the bacterial cells of step (b) indicates upregulated expression of the nucleotide sequence.
13. The method of embodiment 10, 11, or 12, wherein the DVU2956 sigma 54-dependent EBP regulatory sequence comprises a promoter sequence.
14. The method of embodiment 10, 11, 12, or 13, wherein the bacterial cells or other bacteria cells are sulfate-reducing bacteria (sulfide-producing bacteria) cells.
15. The method of embodiment 10, 11, 12, 13, or 14, comprising screening a plurality of test compounds by following steps (a)-(c) to identify one or more candidate compounds for controlling bacteria cells.
16. A polynucleotide comprising (i) a DVU2956 sigma 54-dependent enhancer-binding protein (EBP) regulatory sequence operably linked to (ii) a nucleotide sequence, wherein the regulatory sequence and the nucleotide sequence are heterologous to each other, optionally wherein the regulatory sequence includes a promoter sequence.
17. A cell comprising the polynucleotide of embodiment 16, optionally wherein the nucleotide sequence is capable of being expressed by the cell, and preferably wherein the cell is a bacterial cell.

EXAMPLES

The present disclosure is further exemplified in the below Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Materials and Methods

Bacterial Strains and Growth Conditions

| Strains | Features[a] | Source |
| --- | --- | --- |
| D. vulgaris Hildenborough | Wild-type, ATCC 29579 | American Type Culture Collection (ATCC) |
| D. desulfuricans | Wild-type, isolated from sulfidic mud, DSM 12129 | Deutsche Sammlung von Mikroorganismen und Zellkulturen GmbH (DSMZ) |

| Strains | Features[a] | Source |
|---|---|---|
| E. coli TG1 | K-12 supE thi-1 Δ(lac-proAB) Δ(mcrB- hsdSM)5, ($r_K^- m_K^-$) | J. Minshull |
| E. coli BL21(DE3) | F⁻ ompT hsdS$_B$($r_B^- m_B^-$) gal dcm (DE3) | M. Nomura |

*Desulfovibrio vulgaris* Hildenborough (ATCC 29579) was grown anaerobically at 30° C. in 25-mL screwcap tubes containing 10 mL of modified Baar's medium (ATC® Medium 1249; ~166 mM MgSO$_4$, ~19 mM sodium citrate, ~7 mM CaSO$_4$, ~19 mM NH$_4$Cl, ~3 mM K$_2$HPO$_4$, ~31 mM sodium lactate, ~1 g/L yeast extract, pH 7.5) with 0.025% sodium sulfide (as an oxygen scavenger). Initial cultures were grown from glycerol stocks stored at −80° C.; all subcultures were grown from a 5% inoculum from the initial culture and incubated without shaking; 400 ng/μL Geneticin® (G418) was used to maintain plasmids. *E. coli* strains were cultured at 37° C. with shaking at 250 rpm using LB medium with 50 ng/μL kanamycin to maintain broad host vectors based on plasmid pVLT33.

Plasmids and Recombinant Work

DVU2961 (SEQ ID NO:6), DVU2962 (SEQ ID NO:8) and DVU2964 (SEQ ID NO:10) proteins. The DVU2956-encoding sequence was also cloned into plasmid pMQ70, which was used for inducing DVU2956 (SEQ ID NO:2) expression via inducible promotor PBAD.

The native dvu2956 gene in *D. vulgaris* was knocked out using plasmid pBluescriptII®(SK−)−Δdvu2956, which does not replicate. This construct contains upstream (1008 bp) and downstream (915 bp) sequences of dvu2956 that flank a kanamycin-resistance gene derived from vector pBSKan. For complementing *D. vulgaris* (dvu2956⁻) phenotypes, a regulatory sequence (SEQ ID NO:12) comprising dvu2956 promoter (SEQ ID NO:13), herein denoted as "Pdvu2956") and dvu29565'-untranslated region (SEQ ID NO:14) sequences of *D. vulgaris* was cloned into broad-host range

| Plasmids | Features[a] | Source |
|---|---|---|
| pVLT33 | broad-host-range expression vector (IncQ, RSF1010 replicon), Km$^r$, Ptac, lacIq tra⁻ mob⁺ | de Lorenzo et al., 1993, *Gene* 123: 17-24.[b] |
| pBluescriptII® (SK-) | *E. coli* vector, pUC ori, f1 (−) ori, Amp$^r$, Plac | Stratagene |
| pBSKan | *E. coli* vector, pUC ori, f1 (−) ori, Km$^r$, Plac | Canada et al., 2002, *J. Bacteriol.* 184: 344-349.[b] |
| pET-27b(+) | PT7, pBR322 ori, Km$^r$ | Novagen® |
| pMQ70 | PBAD, Car$^r$, shuttle vector for inducible expression using BAD promoter (PBAD) | Shanks et al., 2006, *Appl. Environ. Microbiol.* 72: 5027-5036.[b] |
| pVLT33-Pdvu0304-dvu2956 | Pdvu0304::dvu2956, RSF1010 replicon, Km$^r$, Ptac, lacIq tra⁻ mob⁺ (for expressing DVU2956 [SEQ ID NO: 2] in biofilm cells) | Herein |
| pVLT33-Pdvu0304-dvu2960 | Pdvu0304::dvu2960, RSF1010 replicon, Km$^r$, Ptac, lacIq tra⁻ mob⁺ (for expressing DVU2960 [SEQ ID NO: 4] in biofilm cells) | Herein |
| pVLT33-Pdvu0304-dvu2961 | Pdvu0304::dvu2961, RSF1010 replicon, Km$^r$, Ptac, lacIq tra⁻ mob⁺ (for expressing DVU2961 [SEQ ID NO: 6] in biofilm cells) | Herein |
| pVLT33-Pdvu0304-dvu2962 | Pdvu0304::dvu2962, RSF1010 replicon, Km$^r$, Ptac, lacIq tra⁻ mob⁺ (for expressing DVU2962 [SEQ ID NO: 8] in biofilm cells) | Herein |
| pVLT33-Pdvu0304-dvu2964 | Pdvu0304::dvu2964, RSF1010 replicon, Km$^r$, Ptac, lacIq tra⁻ mob⁺ (for expressing DVU2964 [SEQ ID NO: 10] in biofilm cells) | Herein |
| pVLT33-Ptac-dvu2956 | Ptac::dvu2956, RSF1010 replicon, Km$^r$, lacIq tra⁻ mob⁺ | Herein |
| pBluescriptII® (SK-)-Δdvu2956 | pBluescriptII (SK-)- Δdvu2956 Ω Km$^r$ (for disrupting dvu2956 in *D. vulgaris*) | Herein |

[a]Km$^r$, Amp$^r$ and Car$^r$ indicate kanamycin-, ampicillin- and carbenicillin-resistance, respectively.
[b]Reference is incorporated herein by reference.

A nucleotide sequence encoding *D. vulgaris* DVU2956 sigma 54-dependent EBP (SEQ ID NO:2) was cloned into broad-host range plasmid pVLT33 under the control of the biofilm phase promoter Pdvu0304 (*D. vulgaris*) and ribosome binding site "AAGGAG" to render plasmid pVLT33-Pdvu0304-dvu2956. Similar constructs were made for individually expressing *D. vulgaris* DVU2960 (SEQ ID NO:4), plasmid pMQ70 (replacing PBAD) to render plasmid pMQ70-Pdvu2956. Then, ribosome binding site "AAGGAG" and nucleotide sequence encoding DVU2956 (SEQ ID NO:2) were inserted downstream of Pdvu2956 to render plasmid pMQ70-Pdvu2956-dvu2956. Successful preparation of the plasmid constructs used herein was confirmed by sequencing.

Competent *D. vulgaris* and *D. desulfuricans* cells (turbidity of $OD_{600\ nm}$~0.3) were prepared by washing twice anaerobically with pre-chilled, sterile 10% glycerol. Plasmid DNA (0.5 to 1 µg) was added to the competent cells (50 µL) by mixing gently, and this preparation was transferred to a pre-chilled (0° C.), 1-mm electroporation cuvette in an anaerobic chamber. Electroporation (25 µF, 200Ω, 1.5 kV/cm) was then performed aerobically, and the cuvette was moved back to the anaerobic chamber immediately, where Modified Baar's medium (1 mL) was added. The electroporated cells were mixed gently and transferred to a 1.5-mL Eppendorf® tube where they recovered overnight at 30° C. Recovered cell preparation (50 µL) was then inoculated into either 10 mL of Modified Baar's medium (0.2% yeast extract) or 1% agar plates; both these media contained either G418 (400 µg/mL for *D. vulgaris*, 800 µg/mL for *D. desulfuricans*) or 300 µg/mL carbenicillin for *D. vulgaris*. Genomic DNA from 1-2 mL culture or a colony was isolated using UltraClean® Microbial DNA isolation kit (MO BIO cat. no. 12224) and used for PCR verification of the presence of the correct plasmid in transformed cells.

Biofilm Formation and Maintenance Assays

*D. vulgaris*, *D. desulfuricans* and plasmid-transformed strains of both of these bacteria were grown anaerobically in Modified Baar's medium (300 µL) in 96-well micro-titer plates (Fisher Scientific, cat no. 07-200-656) for 24 hours at 30° C. without shaking, after which time the planktonic cell turbidity in each well was measured spectrophotometrically at 620 nm using a Sunrise™ microplate reader (TECAN, Switzerland). The plates were then incubated under the same conditions for an additional 24 to 48 hours, after which biofilm formation was measured by crystal violet staining. For biofilm dispersal assays, 24 hours after seeding the plates for biofilm growth, arabinose (10 mM) was added to strains harboring plasmids allowing arabinose-based induction of DVU2956 (SEQ ID NO:2). The arabinose-treated strains were then incubated anaerobically for another 24 hours without shaking, after which time biofilm formation was measured by crystal violet staining.

For crystal violet staining, the liquid portion of the cultures was discarded and the wells were washed by dipping the plates into 1 L of distilled water, after which the plates were dried with paper towel. Crystal violet (0.1%, 300 µL) was added to each well and the plates were incubated for 20 minutes at room temperature. After discarding the bulk of the staining solution, the wells were washed three times with distilled water as above to remove unbound crystal violet. The wells were then soaked for 5 minutes in 95% ethanol (300 µL) to dissolve the remaining (bound) crystal violet, which was then measured spectrophotometrically at 540 nm using the Sunrise™ microplate reader. Normalized biofilm formation percentage values were calculated based on the ratio of a sample's respective OD 620 nm reading (initial planktonic cell turbidity) to its OD 540 nm reading (bound crystal violet) to compare the degree of biofilm formation or dispersal.

RNA Analyses by RNA-Seq and qRT-PCR

*D. vulgaris* biofilm and planktonic cells were first grown, after which RNA was isolated from each cell type for further analysis.

Baar's modified medium (300 mL) was inoculated with a *D. vulgaris* culture. The culture was anaerobically incubated at 30° C. for 3 days to an $OD_{600\ nm} \geq 0.3$. Subsequently, 3×400 mL of Baar's modified medium was inoculated with this culture for a starting $OD_{600\ nm}=0.1$. Each of these cultures was then added to a 1-L beaker. Autoclaved glass wool (10 g) was also included in each beaker. The cultures were kept anaerobically standing at 30° C. for 16-24 hours until $OD_{600\ nm}$=~0.2. RNA was then separately isolated from the biofilm and planktonic cells as described below, and used for RNA analysis.

RNA-Seq Comparative transcriptomic analysis of RNA samples (RNA-Seq) was based on normalizing gene transcript sequencing results to Transcripts Per Kilobase Million (TPM). TPM was calculated by first dividing the read counts by the length of each gene in kilobases to yield reads per kilobase (RPK) for each gene. Then the total RPK values of all the genes in a sample were added together and divided by 1000000 to yield a per-million scaling factor. Finally, the RPK value of each gene was divided by this scaling factor to obtain the TPM value of each gene, and so the sum of all the TPMs in each sample was 1000000. This method thus allowed a direct comparison of the transcription of each gene between different samples.

qRT-PCR Prior to performing qRT-PCR, regular PCR with *D. vulgaris* genomic DNA was performed to ensure that only a single band was produced by the primers. The qRT-PCR thermocycling protocol was: 95° C. for 5 min; 40 cycles of 95° C. for 15 s, 60° C. for 1 min (annealing temperature was 60° C. for all primers). Two replicate qRT-PCR reactions were performed for each sample/primer pair. Components from the iTaq™ universal SYBR® Green One-Step kit (Bio-Rad) were used for each reaction.

Bioinformatics

Protein domain analysis was performed using the Conserved Domain Search Service of the National Center for Biotechnology Information (NCBI) website (ncbi.nlm.nih.gov). Sequence alignment was performed using the Basic Local Alignment Search Tool (BLAST) at the NCBI website. Multiple amino acid sequence alignment analysis was conducted using Clustal X2.0 (Larkin et al., 2007, *Bioinformatics* 23: 2947-2948).

Hydrogen Sulfide Production Assay

Hydrogen sulfide ($H_2S$) by *D. vulgaris* strains was measured via a methylene blue spectrophotometric assay (Rabinowitz, 1978, *Methods Enzymol.* 53:275-277; incorporated herein by reference). Briefly, in this assay, N,N-dimethyl-p-phenylenediamine dihydrochloride is converted into methylthioninium chloride (methylene blue) by reacting with $H_2S$ dissolved in hydrochloride acid in the presence of ferric chloride. For a 96-well screening format, *D. vulgaris* was anaerobically grown in Modified Baar's medium in a 96-well plate (starting turbidity/OD of 0.05 at 600 nm, 150-µL culture volume) and incubated for 48 hours for biofilm formation. Anaerobically, 25 µL of each biofilm culture was transferred to another 96-well plate containing 225 µL deoxygenated water per well to render a 10-fold dilution of the transferred culture. Next, 5% N,N-dimethyl-p-phenylenediamine dihydrochloride (24.5 µL, prepared in 5.5 N HCl) (Sigma-Aldrich, cat. no. 536-46-9) was added to each well. After mixing the wells gently by pipetting and anaerobically incubating the mixes at room temperature for 3 minutes, the 96-well plate was removed from the anaerobic chamber and the absorbance at 670 nm of each well was measured using a Sunrise™ microplate reader.

For a more rigorous $H_2S$ assay, sealed glass vials were used to prevent $H_2S$ loss. *D. vulgaris* strains were grown anaerobically for 7 to 10 days in 10 mL of Modified Baar's medium with 2.5 g of sterilized glass wool to promote biofilm formation. Supernatants from these cultures were transferred by syringe to another sealed vial for dilution with 10 mL of PBS buffer. Anaerobically, 1 mL of diluted sample was then transferred by syringe to another sealed bottle with 125 µL of 12% sodium hydroxide and 3.25 mL of 1% zinc acetate (to fix the sulfide from $H_2S$ by forming ZnS precipitates). After mixing gently and incubating for 30 minutes at room temperature, 625 µL of 5% N,N-dimethyl-p-phenylenediamine dihydrochloride and 125 µL 0.023 M $FeCl_3$ were added and the mixture was shaken for 20 minutes at 300 rpm at room temperature. Water (2.125 mL) was added and mixed, and then at least 1 mL of each reaction was removed to determine absorbance at 670 nm.

Example 1

DVU2956 Sigma 54-Dependent Enhancer-Binding Protein (EBP) Gene Expression is Repressed in Bacteria in a Biofilm This Example describes identifying a gene encoding sigma 54-dependent EBP as being repressed by bacteria comprised within a biofilm. In particular, a biofilm of *Desulfovibrio vulgaris*, which is a sulfate-reducing bacteria, was found to exhibit repressed expression of DVU2956 sigma 54-dependent EBP.

To identify genes involved in bacteria biofilm maintenance and/or formation, RNA-Seq analysis (whole transcriptome shotgun sequencing analysis) was performed to compare the transcription of biofilm cells versus planktonic cells (i.e., floating as single cells) of *Desulfovibrio vulgaris* Hildenborough (American Type Culture Collection [ATCC®] No. 29579). To prepare each of these types of cells, *D. vulgaris* was inoculated into Modified Baar's medium and incubated anaerobically at 30° C. for 16-24 hours in beakers containing glass wool until $OD_{600\ nm}$=~0.2. The glass wool was collected from the beakers and quickly washed with an RNase-free 0.85% NaCl solution. Biofilm cells were released from the glass wool by sonication and then collected in a centrifuge tube by centrifugation at −2° C. for 2 minutes (8200 rpm). Planktonic cells, which were left behind in the medium after glass wool removal and at exponential growth phase, were also collected using centrifugation. Each set of collected cells was individually resuspended in pre-chilled RNAlater™ solution (Thermo Fisher Scientific) and chilled for 5 seconds in a dry ice/ethanol bath. The chilled cells were then centrifuged for 15 seconds at 13000 rpm, after which the collected cells were flash-frozen in the dry ice/ethanol bath. Total RNA samples of the biofilm and planktonic cells (each in triplicate) were prepared using the High Pure RNA Isolation Kit (Roche).

The total RNA samples were then entered into RNA-Seq for transcriptional quantification and comparison. Transcript sequencing results were normalized on a Transcripts Per Kilobase Million (TPM) basis, thereby allowing a direct comparison of the transcription of each gene in the *D. vulgaris* biofilm cells versus the *D. vulgaris* planktonic cells. This comparison showed, for example, that expression of the sigma 54-dependent EBP, DVU2956 (SEQ ID NO:2), is repressed in biofilm cells relative to expression of this EBP in planktonic cells (Table 2). The average TPM for DVU2956 in biofilm cells was about 8.9, thereby reflecting about a 25-fold reduction in DVU2956 expression as compared to its expression in planktonic cells (TPM=222.9).

TABLE 2

Highly Repressed *D. vulgaris* Genes in Biofilm Cells Relative to Expression by Planktonic Cells

| Gene ID | Gene Name | Average TPM in Planktonic Cells | Fold Difference in Biofilm Cells[a] | Protein Length (aa) |
|---|---|---|---|---|
| DVUA0144 | | 5523.7 | −∞ | 47 |
| DVUA0134 | | 4552.2 | −∞ | 343 |
| DVUA0014 | | 3189.2 | −∞ | 108 |
| DVUA0122 | | 2988.9 | −∞ | 216 |
| DVUA0010 | | 2680.3 | −∞ | 100 |
| DVUA0009 | | 2233.7 | −∞ | 568 |
| DVUA0128 | | 2054.2 | −∞ | 48 |
| DVUA0012 | | 2038.2 | −∞ | 542 |
| DVUA0119 | | 1782.7 | −∞ | 438 |
| DVUA0065 | | 1773.8 | −∞ | 678 |
| DVUA0096 | | 1731.1 | −∞ | 403 |
| DVUA0121 | | 1695.3 | −∞ | 484 |
| DVUA0060 | | 1503.5 | −∞ | 461 |
| DVUA0125 | | 1492.9 | −∞ | 450 |
| DVUA0083 | | 1460.8 | −∞ | 42 |
| DVUA0045 | | 1427.7 | −∞ | 538 |
| DVUA0102 | | 1392.8 | −∞ | 271 |
| DVUA0044 | | 1076.4 | −∞ | 325 |
| DVUA0113 | | 1074.0 | −∞ | 602 |
| DVUA0149 | | 1062.9 | −∞ | 594 |
| DVUA0046 | | 1004.2 | −∞ | 482 |
| DVUA0008 | | 898.1 | −∞ | 504 |
| DVU3321 | | 398.1 | −∞ | 30 |
| DVU2605 | | 360.6 | −∞ | 144 |
| DVU1297 | | 318.9 | −∞ | 50 |
| DVU2700 | | 292.2 | −∞ | 139 |
| DVU0205 | | 291.6 | −∞ | 55 |
| DVU2248 | | 287.7 | −∞ | 34 |
| DVU3081 | | 271.4 | −∞ | 300 |
| DVU1275 | | 270.2 | −∞ | 186 |
| DVU0667 | | 263.5 | −∞ | 329 |
| DVU2528 | | 257.4 | −∞ | 65 |
| DVU3361 | | 252.1 | −∞ | 341 |
| DVU0230 | | 250.5 | −∞ | 154 |
| DVU1731 | | 247.2 | −∞ | 56 |
| DVU1127 | | 246.1 | −∞ | 137 |

TABLE 2-continued

Highly Repressed *D. vulgaris* Genes in Biofilm
Cells Relative to Expression by Planktonic Cells

| Gene ID | Gene Name | Average TPM in Planktonic Cells | Fold Difference in Biofilm Cells[a] | Protein Length (aa) |
|---|---|---|---|---|
| DVU3155 | | 235.1 | $-\infty$ | 963 |
| DVU2207 | | 224.3 | $-\infty$ | 57 |
| DVU0001 | | 221.9 | $-\infty$ | 437 |
| DVU2596 | | 218.3 | $-\infty$ | 259 |
| DVU1725 | | 211.2 | $-\infty$ | 202 |
| DVU3166 | | 205.5 | $-\infty$ | 218 |
| DVU3058 | | 205.1 | $-\infty$ | 1223 |
| DVU1790 | | 193.1 | $-\infty$ | 771 |
| DVU1162 | | 191.8 | $-\infty$ | 63 |
| DVU1693 | | 185.8 | $-\infty$ | 324 |
| DVU1052 | | 185.7 | $-\infty$ | 354 |
| DVU1590 | | 183.2 | $-\infty$ | 456 |
| DVU0833 | | 182.2 | $-\infty$ | 134 |
| DVU2790 | | 181.8 | $-\infty$ | 46 |
| DVU2768 | | 80.3 | $-\infty$ | 298 |
| DVU1128 | | 205.7 | −75.6 | 221 |
| DVU2202 | | 223.8 | −9.6 | 505 |
| DVU2239 | disH | 231.9 | −4.0 | 481 |
| DVU2699 | | 121.9 | −95.0 | 215 |
| DVU3205 | | 294.2 | −5.6 | 481 |
| DVU0310 | fliI | 272.6 | −3.3 | 437 |
| DVU0311 | | 191.9 | −1.5 | 250 |
| DVU0312 | fliG | 340.9 | −1.6 | 338 |
| DVU0313 | fliF | 429.3 | −2.7 | 538 |
| DVU0512 | | 384.7 | −2.0 | 260 |
| DVU0513 | flgG | 258.1 | −1.5 | 260 |
| DVU0514 | | 205.9 | −3.4 | 310 |
| DVU0516 | flgI | 320.6 | −2.6 | 378 |
| DVU0517 | | 228.5 | −2.4 | 610 |
| DVU3231 | | 217.9 | −2.8 | 365 |
| DVU3232 | flhA | 330.4 | −7.0 | 703 |
| DVU3233 | flhB | 255.6 | −5.3 | 357 |
| DVU3234 | | 477.9 | −2.6 | 263 |
| DVU0043 | fliQ | 5110.0 | −1.7 | 89 |
| DVU0044 | fliP | 87.6 | −4.1 | 235 |
| DVU0045 | | 149.9 | −1.6 | 173 |
| DVU0048 | | 186.8 | −5.8 | 246 |
| DVU0050 | motA-1 | 185.5 | −23.4 | 252 |
| DVU0086 | | 951.9 | −40.2 | 73 |
| DVU2269 | | 3760.9 | −16.4 | 55 |
| DVU2687 | | 4449.5 | −11.3 | 176 |
| DVU2167 | | 1010.9 | −8.7 | 69 |
| DVU1733 | | 988.3 | −7.4 | 73 |
| DVU0019 | ngr | 1214.2 | −6.7 | 202 |
| DVU2956 | | 222.9 | −25.0 | 345 |
| DVU1803 | | 141.9 | −5.2 | 362 |
| DVU2732 | | 128.3 | −5.2 | 66 |
| DVU2733 | | 305.9 | −14.3 | 249 |

[a]Provided is the fold-difference (each value is negative) in TPM for each listed gene in *D. vulgaris* biofilm cells as compared to the TPM for the same gene in *D. vulgaris* planktonic cells.

To confirm this RNA-Seq result indicating DVU2956 repression, qRT-PCR was performed with independently prepared RNA samples (above isolation protocol) of *D. vulgaris* biofilm and planktonic cells. The results showed that expression of DVU2956 (SEQ ID NO:2) and DVU2960, which is regulated by DVU2956 (Kazakov et al., 2015, *BMC Genomics* 16:919), were repressed 184-fold and 26.6-fold in biofilm cells, respectively, as compared to planktonic cells.

Amino acid sequence alignment analysis showed that homologs of *D. vulgaris* DVU2956 protein (SEQ ID NO:2) are widely present in sulfate-reducing bacteria, and also present in some other bacteria (Table 3). Based on these observations, it is contemplated that DVU2956 sigma 54-dependent EBP plays a role in biofilm regulation across a wide spectrum of bacterial species.

TABLE 3

Percent Amino Acid Identity of DVU2956 Sigma 54-Dependent
EBP across Sulfate-Reducing Bacteria and Other Bacteria

| Bacteria | DVU2956 Percent Amino Acid Identity[a] |
|---|---|
| *Desulfovibrio vulgaris* str. Hildenborough | 100% |
| *Desulfovibrio vulgaris* DP4 | 100% |
| *Desulfovibrio vulgaris* RCH1 | 100% |
| *Desulfovibrio vulgaris* str. 'Miyazaki F' | 71% |
| *Desulfomicrobium baculatum* DSM 4028 | 57% |
| *Desulfobacterales bacterium* C00003104 | 48% |
| *Desulfococcus multivorans* | 45% |
| *Desulfobacula* sp. RIFOXYB2_FULL_45_6 | 43% |
| *Desulfobacter postgatei* | 44% |
| *Desulfatitalea tepidiphila* | 44% |
| *Desulfotomaculum australicum* | 47% |

TABLE 3-continued

Percent Amino Acid Identity of DVU2956 Sigma 54-Dependent EBP across Sulfate-Reducing Bacteria and Other Bacteria

| Bacteria | DVU2956 Percent Amino Acid Identity[a] |
|---|---|
| *Desulfosporosinus lacus* | 46% |
| *Thermodesulfovibrio aggregans* | 43% |
| *Thermodesulfobacterium commune* | 43% |
| *Thermodesulfatator autotrophicus* | 44% |
| *Desulfotalea psychrophila* | 42% |
| *Syntrophobacter fumaroxidans* | 44% |
| *Clostridium magnum* | 43% |
| *Shigella dysenteriae* | 45% |
| *Escherichia coli* | 45% |
| *Bacillus ligniniphilus* | 47% |
| *Candidatus Moduliflexus flocculans* | 45% |
| *Pseudomonas hussainii* | 45% |
| *Brevibacillus* sp. NRRL NRS-603 | 44% |
| *Klebsiella pneumoniae* KCTC 2242 | 45% |

[a]Percent identity was determined with respect to the DVU2956 sigma 54-dependent EBP of SEQ ID NO: 2.

Example 2

Upregulated Expression of DVU2956 Sigma 54-Dependent EBP in Bacteria Inhibits Biofilm Formation and Maintenance This Example describes that upregulating expression of DVU2956 sigma 54-dependent EBP in bacteria inhibits biofilm formation by planktonic cells and disperses cells that have already formed a biofilm. In particular, upregulated expression of DVU2956 sigma 54-dependent EBP in *D. vulgaris* was found to induce these features. This upregulated expression was also shown to inhibit biofilm formation by *Desulfovibrio desulfuricans*. This Example further describes that upregulated expression of DVU2960, DVU2962 and DVU2964 proteins similarly inhibits bacterial biofilm formation.

*D. vulgaris*, *D. desulfuricans* and certain plasmid-transformed strains of both of these bacteria were grown and analyzed for biofilm formation and maintenance as described above (Materials and Methods). By utilizing a promoter from gene dvu0304 that is active only in biofilms, it was found that biofilm formation (at 48 hours) by *D. vulgaris* harboring construct pVLT33-Pdvu0304-dvu2956 (which drives expression of DVU2956 [SEQ ID NO:2] in biofilm cells) was inhibited by −70% as compared to negative controls (wild type *D. vulgaris* and *D. vulgaris*/pVLT33-Pdvu0304) (FIG. 1). This experiment was performed four times with consistent results. Further work demonstrated that knocking out the native dvu2956 gene in *D. vulgaris*, which rendered *D. vulgaris* (dvu2956−), increased biofilm formation by 30.1±0.6% compared to wild type *D. vulgaris* (FIG. 1). When *D. vulgaris* (dvu2956−) was complemented with plasmid pMQ70-Pdvu2956-dvu2956, biofilm formation (at 24 hours) was inhibited by 48±11% as compared to control strain *D. vulgaris* (dvu2956−)/pMQ70-Pdvu2956 (FIG. 1). Further, by using broad host range vector pMQ70 to express DVU2956 (SEQ ID NO:2) from an inducible promoter (PBAD), induction of DVU2956 expression in established *D. vulgaris* biofilms was shown to disperse the biofilms after 24 hours by 42±4% as compared to negative control (*D. vulgaris*/pMQ70).

Because DVU2956 sigma 54-dependent EBP regulates the genes dvu2957-dvu2964, which constitute the target operon of DVU2956, direct expression of some of these genes (dvu2960, dvu2961, dvu2962, dvu2964) was tested for their effect on biofilm formation by *D. vulgaris*. It was found that biofilm-specific production (via using pVLT33-Pdvu0304-based constructs) of DVU2960 (SEQ ID NO:4), DVU2962 (SEQ ID NO:8) and DVU2964 (SEQ ID NO:10) proteins in *D. vulgaris* led to 95%, 90% and 45% inhibition of biofilm formation (at 48 hours), respectively, as compared to negative controls (wild type *D. vulgaris* and *D. vulgaris*/pVLT33-Pdvu0304) (FIG. 1).

The effect of DVU2956 sigma 54-dependent EBP in another sulfate-reducing bacteria, *Desulfovibrio desulfuricans* (DSM 12129), was tested. It was found that, similar to the effects observed in *D. vulgaris*, DVU2956 upregulation inhibited biofilm formation (at 24 hours) by 78±9% in *D. desulfuricans*/pVLT33-Pdvu0304-dvu2956 as compared to negative control (*D. desulfuricans*/pVLT33-Pdvu0304) (FIG. 1). Hence, DVU2956 functions in different species of sulfate-reducing bacteria.

Example 3

Upregulated Expression of DVU2956 Sigma 54-Dependent EBP in Bacteria Controls Hydrogen Sulfide Production This Example describes that upregulation of DVU2956 sigma 54-dependent EBP expression controls hydrogen sulfide ($H_2S$) production in sulfate-reducing bacteria. In particular, this feature was observed in *D. vulgaris* with upregulated expression of DVU2956 sigma 54-dependent EBP.

$H_2S$ production assays were performed with *D. vulgaris* strains as described above (Materials and Methods). As observed in 96-well culture conditions, *D. vulgaris* biofilm-specific expression of DVU2956 (SEQ ID NO:2) (*D. vulgaris*/pVLT33-Pdvu0304-dvu2956) decreased $H_2S$ production by 51±2% as compared to negative control (*D. vulgaris*/pVLT33-Pdvu0304), and knock-out of the native dvu2956 gene increased $H_2S$ production by 131±5% as compared to negative control (wild type *D. vulgaris*) (FIG. 2). Verifying these results using sealed vials, it was found that biofilm-specific expression of DVU2956 (SEQ ID NO:2) inhibited $H_2S$ production by 34.6±0.6%, and knock-out of the native dvu2956 gene increased $H_2S$ production by 136±3% (FIG. 2). This latter phenotype of *D. vulgaris* (dvu2956−) could be complemented via ectopic production of DVU2956 (SEQ ID NO:2): $H_2S$ production in *D. vulgaris* (dvu2956)/pMQ70-Pdvu2956-dvu2956 was decreased by 45±13% compared to negative control *D. vulgaris* (dvu2956−)/pMQ70-Pdvu2956 (FIG. 2). These results all consistently demonstrate that DVU2956 sigma 54-dependent EBP expression reduces $H_2S$ production.

Example 4 dvu2956 Gene Regulatory Sequence can be Used to Assay for Modes of Upregulating DVU2956 Sigma 54-Dependent EBP Expression in Bacteria This Example demonstrates that a regulatory sequence of gene dvu2956 can be used to assay for conditions that upregulate expression of DVU2956 sigma 54-dependent EBP in bacteria. A dvu2956 promoter sequence from *D. vulgaris* was tested for this purpose. This tool will be useful for identifying small molecules, and/or other compositions and conditions, that upregulate dvu2956 gene expression in bacteria, thereby controlling bacterial biofilm formation and $H_2S$ production.

A *D. vulgaris* dvu2956 gene regulatory sequence (SEQ ID NO:12), which comprises (in 5' to 3' direction) predicted promoter (SEQ ID NO:13) and 5'-untranslated region (5'-UTR) sequences (SEQ ID NO:14), was linked upstream of a synthetic ribosome binding site (RBS, SEQ ID NO:15) and a codon-optimized nucleotide sequence (SEQ ID NO:16) encoding a monomeric yellow-green fluorescent protein (mNeonGreen™, GenBank® Accession No. KC295282). This nucleotide sequence (provided as SEQ ID NO:17) was constructed in *E. coli* TG1 to render plasmid construct pMQ70-Pdvu2956-mNeonGreen (8164 bp) and then transferred into *D. vulgaris* (wild type) and *E. coli* strain BL21 (DE3), the latter of which was already transformed with plasmid pET27b-dvu2956 (pET27b-dvu2956 allows for IPTG-induced expression of ectopic DVU2956 [SEQ ID NO:2]). PCR analyses confirmed the presence of plasmids pMQ70-Pdvu2956-mNeonGreen (in both strains) and pET27b-dvu2956 (in *E. coli*). Additional *D. vulgaris* and *E. coli* strains that were transformed with plasmid pMQ70 were prepared, and served as negative controls in the fluorescence assays described below.

A comparison of the fluorescence signal of 10-day cultures of planktonic *D. vulgaris* cells showed that *D. vulgaris*/pMQ70-Pdvu2956-mNeonGreen had a fluorescence that was 2.4 fold-higher than that of *D. vulgaris*/pMQ70 (negative control) at 425 nm excitation and 517 nm emission (FIG. 3). This result indicates that Pdvu2956 can heterologously drive gene expression in sulfate-reducing bacterial cells, and therefore is contemplated to be useful as a means for assaying compositions (e.g., small molecules) and/or conditions that upregulate expression of DVU2956 sigma 54-dependent EBP in these cells.

A similar analysis was conducted to test whether Pdvu2956 can heterologously drive gene expression in bacteria other than sulfate-reducing bacteria. A culture of *E. coli*/pMQ70-Pdvu2956-mNeonGreen/pET27b-dvu2956 exhibited several fold higher fluorescence as compared to negative control (*E. coli*/pMQ70/pET27b-dvu2956) (FIG. 4, 0 mM IPTG). This result indicates that Pdvu2956 can heterologously drive gene expression in other types of bacterial cells. Pdvu2956 therefore is contemplated to be a useful tool for assaying compositions (e.g., small molecules) and/or conditions that upregulate expression of DVU2956 sigma 54-dependent EBP in sulfate-reducing bacteria. It was further observed that ectopic expression of DVU2956 (SEQ ID NO:2) as induced by IPTG exposure for 90 minutes resulted in up to about a 14-fold higher fluorescence signal in *E. coli*/pMQ70-Pdvu2956-mNeonGreen/pET27b-dvu2956 as compared to negative control (FIG. 4, 1 mM IPTG). This result shows that DVU2956 protein expression possibly upregulates Pdvu2956 activity.

What is claimed is:

1. A method of identifying a candidate compound for controlling bacteria cells, said method comprising:
   (a) providing bacteria cells comprising a polynucleotide that comprises (i) a DVU2956 sigma 54-dependent enhancer-binding protein (EBP) regulatory sequence operably linked to (ii) a nucleotide sequence;
   (b) contacting the bacteria cells of step (a) with at least one test compound; and
   (c) determining whether expression of said nucleotide sequence by the bacteria cells of step (b) is upregulated, wherein such upregulation indicates that the test compound is a candidate compound for (i) controlling biofilm maintenance or biofilm formation by said bacteria cells or other bacteria cells, and/or (ii) reducing hydrogen sulfide formation by said bacteria cells or other bacteria cells.

2. The method of claim 1, further comprising:
   (d) contacting said bacteria cells or other bacteria cells comprised in a biofilm with the candidate compound identified in step (c), wherein dispersal of the biofilm indicates that the candidate compound inhibits biofilm maintenance;
   (e) contacting said bacteria cells or other bacteria cells comprised in a liquid culture with the candidate compound identified in step (c), wherein an inability of the bacteria cells or other bacteria cells to form a biofilm indicates that the candidate compound inhibits biofilm formation; or
   (f) contacting said bacteria cells or other bacteria cells with the candidate compound identified in step (c), wherein a reduction in hydrogen sulfide production by the bacteria cells or other bacteria cells indicates that the candidate compound inhibits hydrogen sulfide production by the bacteria cells or other bacteria cells.

3. The method of claim 1, wherein said nucleotide sequence comprises a sequence that encodes a reporter protein, wherein increased expression of the reporter protein by the bacterial cells of step (b) indicates upregulated expression of said nucleotide sequence.

4. The method of claim 1, wherein the DVU2956 sigma 54-dependent EBP regulatory sequence comprises a promoter sequence.

5. The method of claim 1, wherein said bacterial cells or other bacteria cells are sulfate-reducing bacteria (sulfide-producing bacteria) cells.

6. The method of claim 1, comprising screening a plurality of test compounds by following steps (a)-(c) to identify one or more candidate compounds for controlling bacteria cells.

7. The method of claim 1, wherein the polynucleotide is heterologous with respect to the bacteria cells.

8. The method of claim 1, wherein the regulatory sequence is heterologous to the nucleotide sequence.

* * * * *